United States Patent [19]

Reap

[11] Patent Number: 4,534,789

[45] Date of Patent: Aug. 13, 1985

[54] HERBICIDAL O-ALKYLSULFONYLOXY- AND O-ALKYLSULFONYLAMINOBENZENESULFONAMIDES

[75] Inventor: James J. Reap, Wilmington, Del.

[73] Assignee: E. I. Du Pont de Nemours and Company, Wilmington, Del.

[21] Appl. No.: 544,429

[22] Filed: Oct. 21, 1983

Related U.S. Application Data

[60] Division of Ser. No. 368,809, Apr. 15, 1983, Pat. No. 4,435,205, which is a continuation-in-part of Ser. No. 262,813, May 19, 1981, abandoned, which is a continuation-in-part of Ser. No. 168,344, Jul. 11, 1980, abandoned.

[51] Int. Cl.[3] .................. C07D 251/46; C07D 251/52; C07D 251/18; A01N 43/70

[52] U.S. Cl. ......................................... 71/93; 544/211; 544/206; 544/208; 544/182

[58] Field of Search .................... 71/93; 544/211, 206, 544/208

[56] References Cited

U.S. PATENT DOCUMENTS

| | | | |
|---|---|---|---|
| 4,127,405 | 11/1978 | Levitt | 71/93 |
| 4,190,432 | 2/1980 | Levitt | 71/93 |
| 4,479,821 | 10/1984 | Meyer et al. | 544/211 |

*Primary Examiner*—John M. Ford

[57] ABSTRACT

N-(Heterocycliccarbamoyl)arylsulfonamides, such as N-[(4,6-dimethoxypyrimidin-2-yl)aminocarbonyl]-2-hydroxybenzenesulfonamide, methanesulfonate are useful for plant growth retardation, brush control and weed control in crops.

25 Claims, No Drawings

HERBICIDAL O-ALKYLSULFONYLOXY- AND O-ALKYLSULFONYLAMINOBENZENESULFONAMIDES

RELATED APPLICATION

This application is a divisional application of my U.S. Ser. No. 368,809 filed Apr. 15, 1982, now U.S. Pat. No. 4,435,205, which is a continuation-in-part of U.S. Ser. No. 262,813, filed May 19, 1981, now abandoned, which in turn is a continuation-in-part of my copending application U.S. Ser. No. 168,344 filed July 11, 1980 (now abandoned).

BACKGROUND OF THE INVENTION

This invention relates to ortho(sulfonyl)oxybenzene sulfonamides and their use as herbicides.

Netherlands Pat. No. 121,788, published Sept. 15, 1966, teaches the preparation of compounds of Formula (I), and their use as general or selective herbicides:

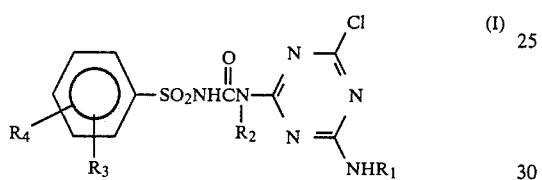

wherein $R_1$ and $R_2$ may independently by alkyl of 1-4 carbon atoms; and $R_3$ and $R_4$ may independently be hydrogen, chlorine or alkyl of 1-4 carbon atoms.

Compounds of Formula (II), and their use as antidiabetic agents, are reported in J. Drug. Res. 6, 123 (1974):

wherein

R is pyridyl.

In U.S. Pat. No. 4,127,405, compounds are disclosed of the general formula:

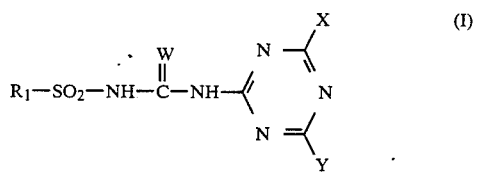

wherein $R_1$ is

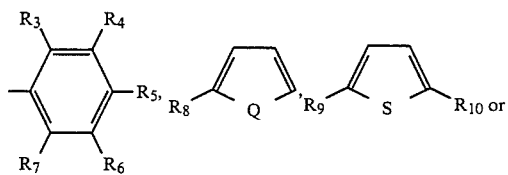

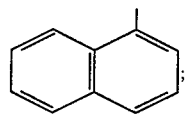

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S-$ or $CH_3OCH_2-$; and Y is methyl or methoxy; or their agriculturally suitble salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses orthosubtituted compounds wherein the substitution is $C_1-C_4$ alkyl.

The presence of undesired vegetation causes substantial damage to useful crops, especially agricultural products that satisfy man's basic food needs, such as soybeans, corn, wheat and the like. The current population explosion and concomitant world food shortage demand improvements in the efficiency of producing these crops. Preventing or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. However, the need exists for still more effective herbicides that destroy or retard weeds without causing significant damage to useful crops.

SUMMARY OF THE INVENTION

This invention relates to novel compounds of Formula I, agriculturally suitable compositions containing them, and their method of use as general as well as selective pre-emergence herbicides.

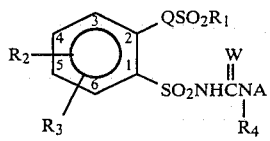 I where
W is O or S;
Q is O or NR$_5$;
R$_1$ is C$_1$-C$_4$ alkyl, C$_1$-C$_4$ alkyl substituted with 1-3 atoms of F, Cl or Br, CH$_2$CH$_2$OCH$_3$, CH$_2$CH$_2$CH$_2$OCH$_3$ or

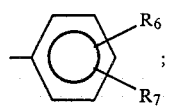

R$_2$ is H, F, Cl, Br, OCH$_3$, NO$_2$, CF$_3$ or C$_1$-C$_2$ alkyl;
R$_3$ is H, F, Cl, Br or CH$_3$;
R$_4$ is H, CH$_3$ or OCH$_3$;
R$_5$ is C$_1$-C$_4$ alkyl;
R$_6$ and R$_7$ are independently H, F, Cl, Br, CH$_3$, CF$_3$, NO$_2$ or OCH$_3$;
A is

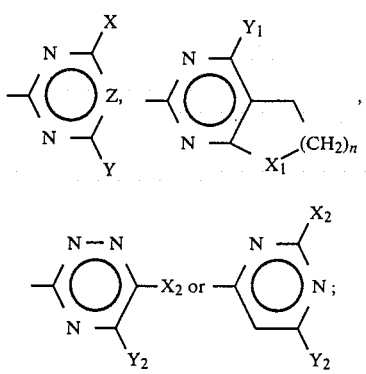

X is NH$_2$, N(CH$_3$)$_2$, NHCH$_3$, C$_1$-C$_4$ alkyl, C$_1$-C$_4$ alkyl substituted with 1-3 atoms of F, Cl or Br, CH$_2$OCH$_3$, CH$_2$OCH$_2$CH$_3$, C$_1$-C$_4$ alkoxy, C$_1$-C$_2$ alkylthio, C$_3$-C$_4$ alkenyloxy, C$_3$-C$_4$ alkynyloxy, OCH$_2$CH$_2$OCH$_3$ or C$_2$-C$_4$ alkoxy substituted with 1-3 atoms of F, Cl or Br;
n is 1 or 2;
Y is H, CH$_3$, OCH$_3$ or Cl;
X$_1$ is O or CH$_2$;
Y$_1$ is H, CH$_3$, OCH$_3$ or Cl;
X$_2$ and Y$_2$ are independently CH$_3$ or OCH$_3$; and
Z is CH, N, CCH$_3$, CBr, CCl, CF, CI, CC$_2$H$_5$, CCH$_2$CH$_2$Cl or CCH$_2$CH=CH$_2$; provided that:
(1) when Y is Cl, then Z is other than N and X is NH$_2$, NHCH$_3$, N(CH$_3$)$_2$, CH$_3$ or OCH$_3$;
(2) when Y is H, then X is OCH$_3$, CH$_3$ or CH$_2$OCH$_3$, and Z is other than N;
(3) when W is S, then R$_4$ is H; and
(4) when R$_4$ is OCH$_3$, then Q is O.

Preferred for reasons of higher herbicidal activity and/or more favorable ease of synthesis are:
(1) Compounds of the generic scope where R$_5$ is CH$_3$, W is O, and R$_4$ is H or CH$_3$;

(2) Compounds of Preferred (1) where R$_1$ is C$_1$-C$_4$ alkyl, CF$_3$, CH$_2$CH$_2$OCH$_3$ or CH$_2$CH$_2$CH$_2$OCH$_3$;
(3) Compounds of Preferred (2) where R$_2$ is H or Cl;
(4) Compounds of Preferred (3) where R$_3$ is H;
(5) Compounds of Preferred (4) where R$_1$ is C$_1$-C$_3$ alkyl or CF$_3$; Q is O; A is

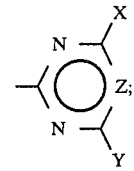

and Z is CH or N;
(6) Compounds of Preferred (5) where R$_4$ is H;
(7) Compounds of Preferred (6) where X and Y are independently CH$_3$ or OCH$_3$, and R$_1$ is CH$_3$; and
(8) Compounds of the generic scope where Q is

R$_5$ is CH$_3$ or CH$_3$CH$_2$;
R$_2$ is C$_1$-C$_3$ alkyl or CF$_3$;
R$_2$ and R$_3$ are H;
X is CH$_3$, OCH$_3$, N(CH$_3$), CH$_2$OCH$_3$, OCH$_2$CH$_3$ or OCH$_2$CF$_3$;
Y is CH$_3$, OCH$_3$ or Cl; and
Z is CH or N.

Specifically preferred for highest herbicidal activity and/or most favorable ease of synthesis are:
N-[(4,6dimethoxypyrimidin-2-yl)aminocarbonyl]-2-hydroxy-5-chlorobenzenesulfonamide methanesulfonate;
N-[(4,6-dimethoxypyrimidin-2-yl)aminocarbonyl]-2-hydroxybenzenesulfonamide, methanesulfonate;
2-hydroxy-N-[(4-methoxy-6-methylpyrimidin-2-yl)aminocarbonyl]benzenesulfonamide, methanesulfonate; and
N-[(4,6-dimethylpyrimidin-2-yl)aminocarbonyl]-2-hydroxybenzenesulfonamide, methanesulfonate.
All of the above compounds show selectivity on wheat.
N-[(4,6dimethoxy-1,3,5-triazin-2-yl)aminocarbonyl]-2-hydroxybenzenesulfonamide, methanesulfonate;
2-hydroxy-N-[(4methoxy-6-methyl-1,3,5-triazin-2-yl)-aminocarbonyl]benzenesulfonamide, methanesulfonate;
N-[(4,6-dimethyl-1,3,5-triazin-2-yl)aminocarbonyl]-2-hydroxybenzenesulfonamide, methanesulfonate;
N-[(4,6-dimethoxy-1,3,5-triazin-2-yl)(methyl)aminocarbonyl]-2-hydroxybenzenesulfonamide, methanesulfonate;
N-[(4,6-dimethoxypyrimidin-2-yl)aminocarbonyl]-2-hydroxybenzenesulfonamide, 1propanesulfonate, which shows selectivity on rice and corn; and
2-hydroxy-N-[(4-methoxy-6-methyl-1,3,5-triazin-2-yl)-aminocarbonyl]benzenesulfonamide, 1- propanesulfonate, which shows selectivity on soybeans.
This invention also relates to compounds of Formula II which are useful intermediates for the preparation of the herbicidal compounds of Formula I:

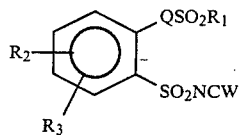

where
W is O or S;
Q is O or NR$_5$;
R$_1$ is C$_1$-C$_4$ alkyl, C$_1$-C$_4$ alkyl substituted with 1-3 atoms of F, Cl or Br, CH$_2$CH$_2$OCH$_3$, CH$_2$CH$_2$CH$_2$OCH$_3$, or

R$_2$ is H, F, Cl, Br, OCH$_3$, NO$_2$ or C$_1$-C$_2$ alkyl;
R$_3$ is H, F, Cl, Br or CH$_3$;
R$_5$ is C$_1$-C$_4$ alkyl; and
R$_6$ and R$_7$ are independently H, F, Cl, Br, CH$_3$, CF$_3$, NO$_2$ or OCH$_3$.

Preferred intermediates, for reasons of more favorable ease of synthesis and/or higher herbicidal activity of the compounds of Formula I, are:

(1) Compounds of Formula II where Q is O, R$_2$ and R$_3$ are H, R$_1$ is CH$_3$ or CF$_3$, and W is O.

This invention also relates to compounds of Formula VII which are useful intermediates for the preparation of the herbicidal compounds of Formula I:

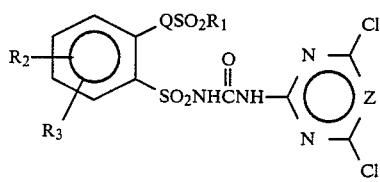

where
Q is O or NR$_5$;
R$_1$ is C$_1$-C$_4$ alkyl, C$_1$-C$_4$ alkyl substituted with 1-3 atoms of F, Cl or Br, CH$_2$CH$_2$OCH$_3$, CH$_2$CH$_2$CH$_2$OCH$_3$, or

R$_2$ is H, F, Cl, Br, OCH$_3$, NO$_2$ or C$_1$-C$_2$ alkyl;
R$_3$ is H, F, Cl, Br or OCH$_3$; R$_5$ is C$_1$-C$_4$ alkyl;
R$_6$ and R$_7$ are independently H, F, Cl, Br, CH$_3$, CF$_3$, NO$_2$ or OCH$_3$; and
Z is CH or N.

Synthesis

The compounds of this invention can be made as outlined below. The compounds of Formula (IV), (VI), (XII) or (XIV) in which Q is oxygen can be prepared by reacting an appropriate 2-aminopyrimidine, 2-aminotriazine or 2-aminobicyclopyrimidine of Formula (III), (V), (XI) or (XIII) with an appropriately substituted sulfonylisocyanate or isothiocyanate, of Formula (II), where Q is oxygen and R$_1$, R$_2$, R$_3$, R$_4$, X, Y, Z, X$_1$, X$_2$, Y$_1$, Y$_2$, W and n are as previously defined.

The reaction is best carried out in inert solvents such as methylene chloride and acetonitrile. The mode of addition is not critical, however, it is often convenient to add a solution of the isocyanate or isothiocyanate of Formula (II) to a stirred suspension of the aminoheterocycle (III), (V), (XI) or (XIII).

The reaction is generally exothermic. In some cases, the desired product is insoluble in the reaction medium and crystallizes from it in pure form. Products soluble in the reaction medium are isolated by evaporation of the solvent and trituration of the residue with solvents such as diethyl ether, 1-chlorobutane, or hexanes and filtration.

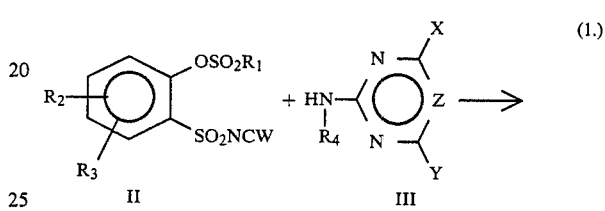

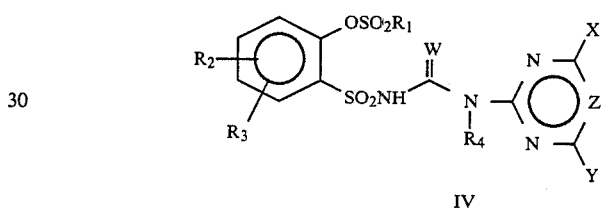

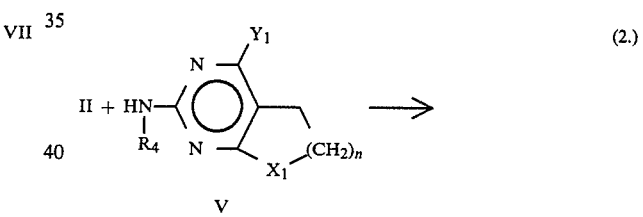

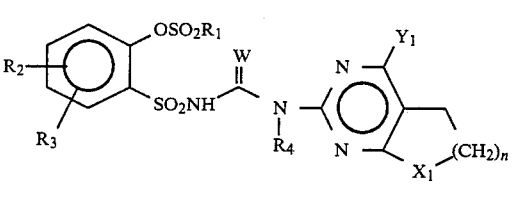

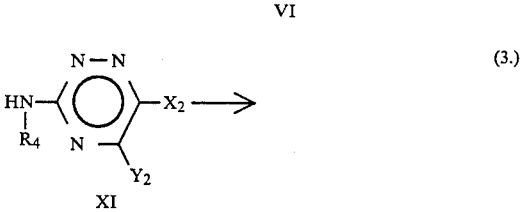

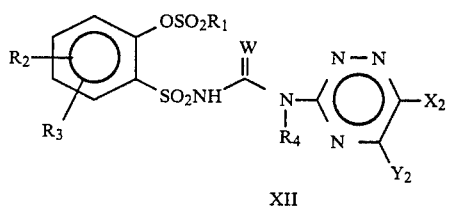

-continued (4.) 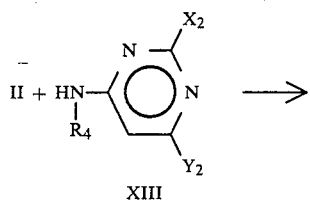

XIII

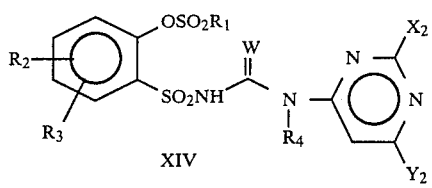

XIV

Some of the compounds of this invention, where Z is CH or N, may also be prepared by reacting a sulfonamide of Formula VIII with a 4,6-dichloroheterocyclic isocyanate of Formula IX.

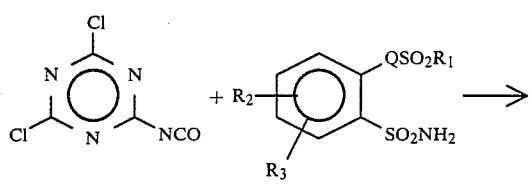

IX        VIII

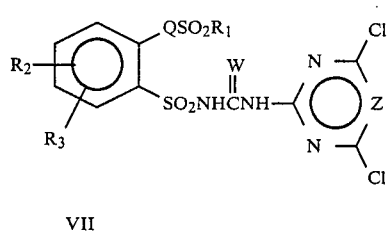

VII

One or both of the halogen atoms on the heterocyclic ring of the compound of Formula VII can be displaced by an alkoxide of $OR_8$, to give compounds of Formula X, where $R_8$ is $C_1$–$C_4$ alkyl, $C_3$–$C_4$ alkenyl, $C_3$–$C_4$ alkynyl, $CH_2CH_2OCH_3$ or $C_2$–$C_4$ alkyl substituted with 1–3 atoms of F, Cl or Br, and Y" is Cl or $OCH_3$.

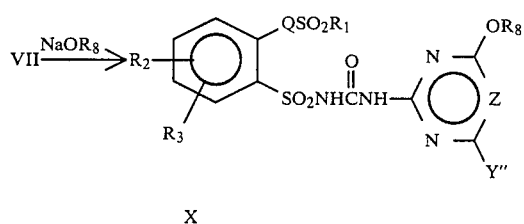

X

The process for the preparation of compounds of Formula X is described in our patent application Ser. No. 193,190, filed Oct. 14, 1980.

Compounds of Formula IV, VI, XII and XIV in which Q is

are best prepared by the procedure of Equation 5 wherein $R_1$, $R_2$, $R_3$, $R_4$, $R_5$ and A are as previously defined.

(5.) 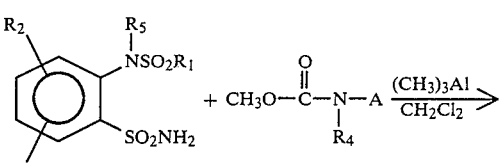

VIII        XV

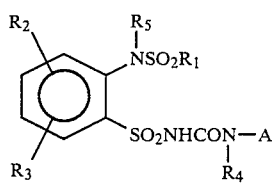

XVI

The reaction of Equation 5 is best carried out in methylene chloride at 25° to 40° C. for 24 to 96 hours under a nitrogen atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride or ether or by column chromatography.

Further details of this reaction and the preparation of the carbamates of Formula III can be found in unexamined European Patent Application 174–73.

Sulfonamides of Formula VIII in which Q is

are readily prepared as shown by Equations 6 and 7.

(6.) 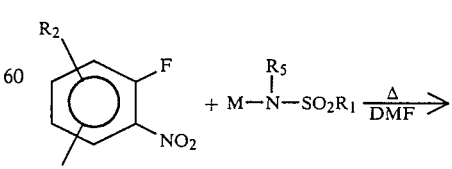

XVII        XVIII

-continued

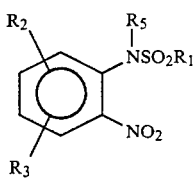

XIX

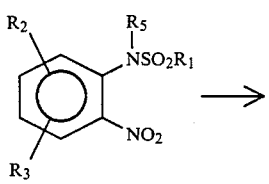

XIX

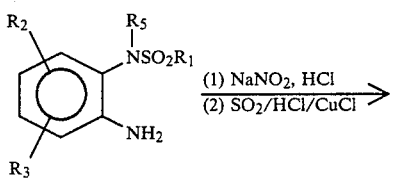

XX

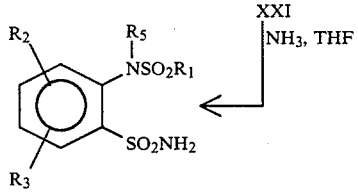

VIII

M is an alkali metal.

The reaction of Equation 6 is carried out in an aprotic solvent such as dimethylformamide at temperatures ranging from about ambient to reflux for periods ranging from ¼ to 24 hours.

The product is isolated by removing the solvent at reduced pressure and pouring the reaction mixture into H₂O. The crude product is extracted with an organic solvent such as methylene chloride. The solution of the product is dried with a standard drying agent such as MgSO₄, filtered, and concentrated. The crude product is further purified by usual techniques such as recrystallization or chromatography.

The reduction of the nitro compounds such as XIX to anilines XX is achieved by procedures well known to those skilled in the art.

Anilines of Formula XX are converted to sulfonyl chlorides by well known procedures. For further details, see H. L. Yale and F. Sowinski, J. Org. Chem., 25, 1824 (1960).

Sulfonamides of Formula VIII in which Q is

are obtained by treatment of sulfonyl chlorides of Formula XXI with NH₃ by procedures known to those skilled in the art.

Sulfonamides of Formula VIII in which Q is oxygen, prepared as described in Research Disclosure, pg. 52, (1978), may conveniently be converted to the corresponding isocyanates or isothiocyanates of Formula II by methods described in U.S. Pat. No. 4,127,405.

The synthesis of the heterocyclicamine derivatives has been reviewed in "The Chemistry of Heterocyclic Compounds", a series published in Interscience Publ., New York and London.

2-Aminopyrimidines are described by D. J. Brown in "The Pyrimidines", Vol. XVI of the above series which are herein incorporated by reference.

The preparation of amino bicyclopyrimidines are described in unexamined European Pat. No. 15683.

The aminoheterocyclic intermediates of Formula III, V, XI or XIII in which R₄ is CH₃, may be prepared by the following procedure, or by obvious modifications thereof.

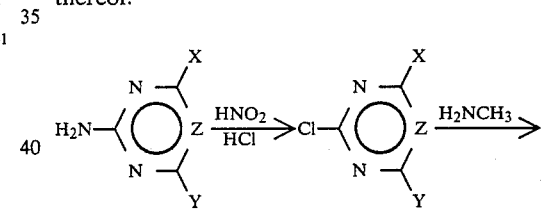

XV      XVI

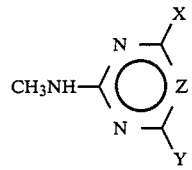

XXIV

A solution of the amine XV in concentrated hydrochloric acid is contacted with an aqueous sodium nitrite solution and the chloro compound XVI is isolated by filtration of the acidic solution (see for example, Bee and Rose, J. Chem. Soc. C., 2051 (1966) for the case in which Z is CH and X and Y are OCH₃). Displacement of the chlorine may be accomplished by heating with an excess of methylamine in water to obtain the methylaminoheterocycle XXIV.

N-Methoxyamino heterocycles can be prepared by procedures reported in the literature [see, for example, Belgian Pat. No. 618,563 and J. T. Shaw, et al., J. Org.

Chem., 27 4054 (1962)] and the procedure illustrated below.

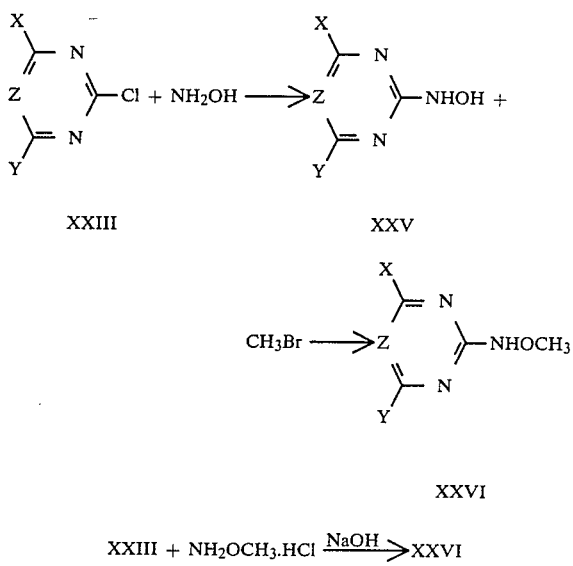

XXIII + NH₂OCH₃.HCl $\xrightarrow{\text{NaOH}}$ XXVI

Chloro compound XXIII is reacted with hydroxylamine to form derivative XXV which may be alkylated with methyl bromide to afford the N-methoxy heterocyclic amine XXVI. This compound may alternately be prepared in one step by treatment of XXIII and O-methyl hydroxylamine hydrochloride with an alkali metal hydroxide such as sodium hydroxide.

The compounds of this invention and their preparation are further illustrated by the following examples, wherein temperatures are given in degrees centigrade and parts are by weight unless otherwise indicated.

EXAMPLE 1

2-Hydroxybenzenesulfonyl isocyanate, methanesulfonate

To 10.0 g (0.04 mole) 2-hydroxybenzenesulfonamide, methanesulfonate, suspended in 75 ml dry xylenes was added 4.0 g (0.04 mole) N-butylisocyanate and a catalytic amount of 1,4-diazobicyclo[2.2.2]-octane (~0.05 g). This mixture was rapidly heated to reflux temperature (~135° C.) and 4.0 ml of phosgene was slowly added (at such a rate as to keep the reaction temperature greater than 128° C.). The phosgene addition required ~1½ hours. The reaction was cooled to room temperature, filtered under N₂, and the solvent evaporated under reduced pressure. The infrared spectrum of the resultant oil was consistent for 2-hydroxybenzenesulfonyl isocyanate, methanesulfonate (2210 cm⁻¹).

EXAMPLE 2

N-[(4,6-Dimethoxypyrimidin-2-yl)aminocarbonyl]-2-hydroxybenzenesulfonamide, methanesulfonate To a suspension of 0.6 g 2-amino-4,6-dimethoxypyrimidine in 10 ml dry methylene chloride is added 1.1 g 2-hydroxybenzenesulfonylisocyanate, methanesulfonate. The reaction exotherms (21° C.-29° C.) and is then stirred ½ hour. The solvent is evaporated under reduced pressure. The resultant mixture is triturated with diethylether and filtered to give 1.2 g tan solid m.p. 165°-166° C. The infrared spectrum shows absorption bands at 1740, 1615, 1590, 1360 cm⁻¹.

Calc. for C—38.9, H—3.73, N—12.9. Found C—38.3, H—3.63, N—13.0.

EXAMPLE 3

2-Hydroxy-N-[(4-methoxy-6-methylpyrimidin-2-yl)aminocarbonyl]benzenesulfonamide, methanesulfonate To a suspension of 0.6 g 2-amino-4-methoxy-6-methylpyrimidine in 10 ml dry methylene chloride is added 1.1 g 2-hydroxybenzenesulfonylisocyanate, methanesulfonate. The reaction exotherms mildly and is then stirred for ½ hour. The solvent is evaporated under reduced pressure. The resultant mixture is triturated with diethylether and filtered to give 0.95 g white solid m.p. 189°-190° C. The infrared spectrum shows absorption bands at 1700, 1615, 1560, 1370 cm⁻¹.

Calc. for C—40.4, H—3.87, N—13.4. Found C—40.2, H—3.77, N—13.6.

EXAMPLE 4

N-[(4,6-dimethoxy-1,3,5-triazin-2-yl)aminocarbonyl]-2-hydroxybenzenesulfonamide, methanesulfonate To a suspension of 0.6 g 2-amino-4,6-dimethoxy-1,3,5-triazine in 10 ml dry methylene chloride is added 1.1 g 2-hydroxybenzenesulfonylisocyanate, methanesulfonate. The reaction exotherms mildly and is then stirred for about 1 hour. The solvent is evaporated under reduced pressure. The resultant mixture is triturated with diethylether and filtered to give 1.4 g tan solid m.p. 163°-166° C. The infrared spectrum shows absorption bands at 1715, 1600, 1550, 1350 cm⁻¹.

EXAMPLE 5

Preparation of N-methyl-N-(2-nitrophenyl)methanesulfonamide

To 3.2 g of N-methyl methanesulfonamide in 50 ml of dry dimethylformamide is added 1.47 g of potassium methoxide. The mixture is stirred for 15 minutes. 2.8 g of 2-Fluoronitrobenzene is added and the mixture is heated to reflux for two hours. The dimethylformamide is removed on a rotary evaporator. The concentrated reaction mixture is poured into water. The crude product is extracted with CH₂Cl₂. The crude extracts are dried with MgSO₄, filtered and concentrated on a rotary evaporator. The crude product is purified by recrystallization from butyl chlorideethyl acetate. 3.4 g of product with m.p. 144°-145° C. is obtained.

EXAMPLE 6

N-(2-Aminophenyl)-N-methyl methanesulfonamide 50.2 g of N-methyl-N-(2-nitrophenyl)methanesulfonamide, prepared by the procedure of Example 5, is added to 220 ml of concentrated HCl and contacted with 183.3 g of SnCl₂.2H₂O. The mixture is heated on a steam bath for one hour. The reaction mixture is treated with enough 5-10% NaOH to raise the pH to 9 while maintaining the temperature of the mixture less than 25° C. The crude reaction mixture is then extracted with CH₂Cl₂. The CH₂Cl₂ extracts are dried with MgSO₄ and then filtered and concentrated on a rotary evaporator. The solid product obtained (38.1 g), m.p. 138°-139° was used without further purification in the next step.

EXAMPLE 7

2-[N-methyl-N-(methylsulfonyl)amino]benzenesulfonamide

Diazotization 20.0 g of amine from Example 6 is combined with 50 ml of acetic acid, 30 ml of H₂O and 39.4 g of concentrated aqueous hydrochloric acid; the mixture is cooled to 0°–5° C. A solution of 7.2 g of NaNO₂ in 20 ml of H₂O is added dropwise over a period of 15–30 minutes, while maintaining the temperature. The reaction mixture is stirred for 30 minutes at 0°–10° C. and then used in the subsequent coupling step.

Coupling

The diazonium salt from the preceding step is added dropwise over 15–30 minutes to a solution of 22.3 ml SO₂, 350 ml of acetic acid and 1.35 g of CuCl cooled to 12°–15° C. After the addition is completed the reaction is stirred at 10°–15° C. for one hour. The cooling bath was removed and the reaction mixture was stirred at ambient temperature for 12 hours. The crude reaction mixture was then poured into water and extracted with ether. The ether extract was backextracted with H₂O and then dried with MgSO₄, filtered and concentrated to the wet solid sulfonyl chloride which was used in the next step without further purification.

Amination

The crude product from the preceding step was taken up in 175 ml of tetrahydrofuran and cooled to 0°–5° C. 75 ml of concentrated aqueous ammonia was added dropwise while maintaining the temperature. The reaction mixture was allowed to warm to ambient temperature over a period of one hour. The crude reaction mixture was poured into water. The crude product was extracted with CH₂Cl₂, dried with MgSO₄, filtered and concentrated on a rotary evaporator. 10.8 g of product with m.p. 137°–139° was obtained and used in the next step without further purification.

EXAMPLE 8

N-[(4,6-dimethoxypyrimidin-2-yl)]-2-[(methyl)(methylsulfonyl)amino]benzenesulfonamide 1.5 g of sulfonamide from Example 8 is added to 60 ml of dry methylene chloride under N₂. 3.6 ml of 2M solution of (CH₃)₃Al in hexane was added. The mixture was stirred for 15 minutes and 1.2 g of

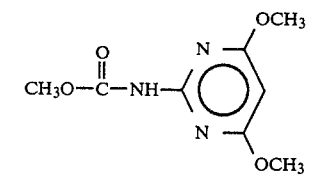

was added. The mixture was refluxed for 16 hours. 50 ml of H₂O was added dropwise cautiously followed by enough acetic acid to lower the pH of the reaction mixture to 2-3. The crude product is then extracted with CH₂Cl₂, dried with MgSO₄, filtered and concentrated on a rotary evaporator. The crude solid product was triturated with butyl chloride-ethyl acetate. 1.2 g of product with m.p. 228°–230° was obtained.

Using the procedures similar to those of Examples 1–8, the following compounds can be prepared.

TABLE I

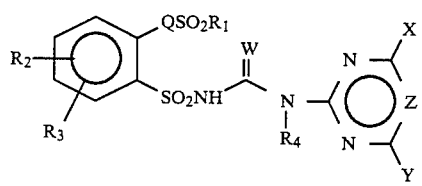

| R₁ | R₂ | R₃ | R₄ | Q | W | Y | X | Z | m.p. (°C.) |
|---|---|---|---|---|---|---|---|---|---|
| CH₃ | H | H | H | O | O | OCH₃ | OCH₃ | CH | 165–166 |
| CH₃ | H | H | H | O | O | OCH₃ | CH₃ | CH | 189–190 |
| CH₃ | H | H | H | O | O | CH₃ | CH₃ | CH | 204–205 |
| CH₃ | H | H | H | O | O | OCH₃ | OCH₃ | N | 163–166 |
| CH₃ | H | H | H | O | O | OCH₃ | CH₃ | N | 170–173 |
| CH₃ | H | H | H | O | O | CH₃ | CH₃ | N | 181–184 |
| (CH₂)₃CH₃ | H | H | H | O | O | OCH₃ | OCH₃ | CH | 158–162 |
| (CH₂)₂CH₂Cl | H | H | H | O | O | OCH₃ | OCH₃ | CH | |
| CCl₃ | H | H | H | O | O | OCH₃ | OCH₃ | CH | |
| 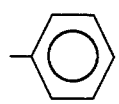 | H | H | H | O | O | OCH₃ | CH₃ | CH | 216–219 |
| 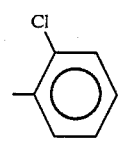 | H | H | H | O | O | OCH₃ | CH₃ | CH | |

TABLE I-continued $$\underset{R_3}{\underset{R_2}{\text{QSO}_2R_1}} \text{SO}_2\text{NH} - \overset{W}{\underset{}{C}} - \underset{R_4}{N} - \underset{N}{\overset{N}{\bigvee}} \overset{X}{\underset{Y}{\bigvee}} Z$$

| R₁ | R₂ | R₃ | R₄ | Q | W | Y | X | Z | m.p. (°C.) |
|---|---|---|---|---|---|---|---|---|---|
| 2,4-dichlorophenyl | H | H | H | O | O | OCH₃ | CH₃ | CH | |
| 2-nitrophenyl | H | H | H | O | O | OCH₃ | CH₃ | CH | |
| 2,5-dimethylphenyl | H | H | H | O | O | OCH₃ | CH₃ | CH | |
| 2,5-bis(CF₃)phenyl | H | H | H | O | O | OCH₃ | CH₃ | CH | |
| 2,4-dibromophenyl | H | H | H | O | O | OCH₃ | CH₃ | CH | |
| 2-OCH₃-4-Cl-phenyl | H | H | H | O | O | OCH₃ | CH₃ | CH | |
| 2,4-difluorophenyl | H | H | H | O | O | OCH₃ | CH₃ | CH | |
| CH₃ | 5-Cl | H | H | O | O | OCH₃ | OCH₃ | CH | 174–176 |
| CH₃ | 6-CH₃ | H | H | O | O | OCH₃ | CH₃ | CH | |
| CH₃ | 5-F | H | H | O | O | OCH₃ | CH₃ | CH | |
| CH₃ | 5-NO₂ | H | H | O | O | OCH₃ | CH₃ | CH | |
| CH₃ | 5-Br | H | H | O | O | OCH₃ | CH₃ | CH | |
| CH₃ | 5-OCH₃ | H | H | O | O | OCH₃ | CH₃ | CH | |
| CH₃ | 5-CF₃ | H | H | O | O | OCH₃ | CH₃ | CH | |
| CH₃ | 5-Cl | 4-Cl | H | O | O | OCH₃ | CH₃ | CH | |
| CH₃ | 5-CH₃ | 4-CH₃ | H | O | O | OCH₃ | CH₃ | CH | |
| CH₃ | H | H | CH₃ | O | O | OCH₃ | OCH₃ | N | 91–96 |

TABLE I-continued

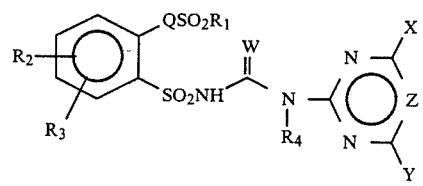

| R₁ | R₂ | R₃ | R₄ | Q | W | Y | X | Z | m.p. (°C.) |
|---|---|---|---|---|---|---|---|---|---|
| CH₃ | H | H | H | —N—CH₃ | O | OCH₃ | OCH₃ | CH | 228–230 |
| CH₃ | H | H | H | —N(CH₂)₃<br>        \|<br>        CH₃ | O | OCH₃ | OCH₃ | CH | |
| CH₃ | H | H | H | O | O | Cl | OCH₃ | CH | |
| CH₃ | H | H | H | O | O | OCH₃ | —(CH₂)₃CH₃ | CH | |
| CH₃ | H | H | H | O | O | CH₃ | —OCH₂CF₃ | N | |
| CH₃ | H | H | H | O | O | CH₃ | —OCH₂CCl₃ | N | |
| CH₃ | H | H | H | O | O | CH₃ | —OCH₂CBr₃ | N | |
| CH₃ | H | H | H | O | O | CH₃ | OCH₂CH₂Cl | N | |
| CH₃ | H | H | H | O | O | CH₃ | H | CH | |
| CH₃ | H | H | H | O | O | CH₃ | (CH₂)₃CH₃ | CH | |
| CH₃ | H | H | H | O | O | CH₃ | —CH₂CH₂Cl | CH | |
| CH₃ | H | H | H | O | O | CH₃ | —CH₂CF₃ | CH | |
| CH₃ | H | H | H | O | O | CH₃ | —O(CH₂)₃CH₃ | N | |
| CH₃ | H | H | H | O | O | CH₃ | —OCH₂CH=CH₂ | N | |
| CH₃ | H | H | H | O | O | CH₃ | —OCH₂C=CH₂<br>           \|<br>           CH₃ | N | |
| CH₃ | H | H | H | O | O | CH₃ | OCH₂C≡CH | N | |
| CH₃ | H | H | H | O | O | CH₃ | OCH₂C≡CCH₃ | N | |
| CH₃ | H | H | H | O | O | CH₃ | —CH₂OCH₃ | CH | |
| CH₃ | H | H | H | O | O | CH₃ | SCH₃ | CH | |
| CH₃ | H | H | H | O | O | CH₃ | S(CH₂)CH₃ | CH | |
| CH₃ | H | H | H | O | O | CH₃ | CH₃ | CBr | |
| CH₃ | H | H | H | O | O | CH₃ | CH₃ | CI | |
| CH₃ | H | H | H | O | O | CH₃ | CH₃ | CF | |
| CH₃ | H | H | H | O | O | CH₃ | CH₃ | CCl | |
| CH₃ | H | H | H | O | S | OCH₃ | OCH₃ | N | |
| CH₃ | H | H | H | O | S | OCH₃ | CH₃ | N | |
| CH₃ | H | H | H | O | S | CH₃ | CH₃ | N | |
| CH₃ | H | H | H | O | S | OCH₃ | CH₃ | CH | |
| CH₃ | H | H | H | O | S | OCH₃ | OCH₃ | CH | |
| CH₃ | H | H | H | O | S | CH₃ | CH₃ | CH | |
| CH₃ | 3-Cl | H | H | O | O | OCH₃ | OCH₃ | CH | 134–142 |
| CH₃ | 3-Cl | H | H | O | O | OCH₃ | OCH₃ | N | 165–170 |
| CH₃ | 3-Cl | 5-Cl | H | O | O | OCH₃ | CH₃ | N | 210(dec) |
| CH₃ | 3-Cl | 5-Cl | H | O | O | OCH₃ | OCH₃ | N | 200(dec) |
| CH₃ | H | H | H | NCH₂CH₃ | O | OCH₃ | OCH₃ | CH | |
| CH₃ | H | H | H | N(CH₂)₂CH₃ | O | OCH₃ | OCH₃ | CH | |
| CH₃ | H | H | H | NCH₃ | O | OCH₃ | CH₃ | CH | 220–222 |
| CH₃ | H | H | H | NCH₃ | O | CH₃ | CH₃ | CH | 216–218 |
| CH₃ | H | H | H | NCH₃ | O | OCH₃ | CH₃ | N | 218–221(d) |
| CH₂CH₃ | H | H | H | O | O | OCH₃ | OCH₃ | CH | 189–191 |
| CH₂CH₃ | H | H | H | O | O | OCH₃ | CH₃ | CH | 160–162 |
| CH₂CH₃ | H | H | H | O | O | CH₃ | CH₃ | CH | 196–198 |
| CH₂CH₃ | H | H | H | O | O | OCH₃ | OCH₃ | N | |
| CH₂CH₃ | H | H | H | O | O | OCH₃ | CH₃ | N | |
| CH₂CH₃ | H | H | CH₃ | O | O | OCH₃ | OCH₃ | N | |
| (CH₂)₃CH₃ | H | H | H | O | O | OCH₃ | OCH₃ | CH | |
| (CH₂)₃CH₃ | H | H | H | O | O | CH₃ | CH₃ | CH | 201–202 |
| (CH₂)₃CH₃ | H | H | H | O | O | OCH₃ | OCH₃ | N | 150–153 |
| (CH₂)₃CH₃ | H | H | H | O | O | OCH₃ | CH₃ | N | 161–163 |
| (CH₂)₃CH₃ | H | H | H | O | O | CH₃ | CH₃ | N | |
| (CH₂)₃CH₃ | H | H | H | O | O | H | CH₃ | CCl | 135–140 |
| (CH₂)₂CH₃ | H | H | H | O | O | OCH₃ | OCH₃ | CH | 172–174 |
| (CH₂)₂CH₃ | H | H | H | O | O | OCH₃ | CH₃ | CH | 183–186 |
| (CH₂)₂CH₃ | H | H | H | O | O | CH₃ | CH₃ | CH | 182–184 |
| (CH₂)₂CH₃ | H | H | H | O | O | OCH₃ | OCH₃ | N | 151–154 |
| (CH₂)₂CH₃ | H | H | H | O | O | OCH₃ | CH₃ | N | 144–147 |
| (CH₂)₂CH₃ | H | H | H | O | O | CH₃ | CH₃ | N | |
| (CH₂)₂CH₃ | H | H | CH₃ | O | O | OCH₃ | OCH₃ | CH | |
| (CH₂)₂CH₃ | H | H | H | O | O | H | CH₃ | CCl | 185–190 |
| CF₃ | H | H | H | O | O | OCH₃ | OCH₃ | CH | 129–131 |
| CH₂CH₂Br | H | H | H | O | O | OCH₃ | OCH₃ | CH | |
| CH₂CH₂OCH₃ | H | H | H | O | O | OCH₃ | OCH₃ | CH | |

TABLE I-continued

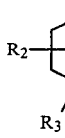

| R₁ | R₂ | R₃ | R₄ | Q | W | Y | X | Z | m.p. (°C.) |
|---|---|---|---|---|---|---|---|---|---|
| CH₂CH₂OCH₃ | H | H | H | O | O | OCH₃ | CH₃ | CH | |
| CH₂CH₂OCH₃ | H | H | H | O | O | CH₃ | CH₃ | CH | |
| CH₂CH₂OCH₃ | H | H | H | O | O | OCH₃ | CH₃ | N | |
| (CH₂)₂CH₂OCH₃ | H | H | H | O | O | OCH₃ | OCH₃ | CH | |
| CH₃ | H | H | H | O | O | Cl | NH₂ | CH | |
| CH₃ | H | H | H | O | O | Cl | NHCH₃ | CH | |
| CH₃ | H | H | H | O | O | Cl | N(CH₃)₂ | CH | |
| CH₃ | H | H | H | O | O | CH₃ | CH₂OCH₃ | CH | |
| CH₂CH₃ | H | H | H | O | O | CH₃ | CH₂OCH₃ | CH | |
| (CH₂)₂CH₃ | H | H | H | O | O | CH₃ | CH₂OCH₃ | CH | |
| CH₃ | H | H | H | O | O | CH₃ | CH₂OCH₂CH₃ | CH | |
| CH₃ | H | H | H | O | O | CH₃ | CH₂CH₃ | CH | |
| CH₃ | H | H | H | O | O | CH₃ | CH₂CH₂CH₃ | CH | |
| CH₃ | H | H | H | O | O | CH₃ | CH₂CH₂Br | CH | |
| CH₃ | H | H | H | O | O | CH₃ | OCH₂CH₃ | CH | |
| CH₃ | H | H | H | O | O | CH₃ | O(CH₂)₂CH₃ | CH | |
| CH₃ | H | H | H | O | O | CH₃ | OCH₂CH=CH₂ | CH | |
| CH₃ | H | H | H | O | O | CH₃ | OCH₂C(CH₃)=CH₂ | CH | |
| CH₃ | H | H | H | O | O | CH₃ | OCH₂C≡CH | CH | |
| CH₃ | H | H | H | O | O | CH₃ | OCH₂C≡CCH₃ | CH | |
| CH₃ | H | H | H | O | O | CH₃ | OCH₂CH₂OCH₃ | CH | |
| CH₃ | H | H | H | O | O | CH₃ | OCH₂CH₂OCH₃ | N | |
| CH₃ | H | H | H | O | O | CH₃ | OCH₂(CH₂)₂Cl | CH | |
| CH₃ | H | H | H | O | O | CH₃ | OCH₂(CH₂)₃Cl | CH | |
| CH₃ | H | H | H | O | O | H | CH₃ | CCl | |
| CH₃ | H | H | H | O | O | Cl | CH₃ | CCH₂CH₂Cl | |
| CH₃ | H | H | H | O | O | OCH₃ | OCH₃ | CH₃ | |
| CH₃ | H | H | H | O | O | OCH₃ | OCH₃ | CH₂CH₃ | |
| CH₃ | H | H | H | O | O | OCH₃ | OCH₃ | CCH₂CH=CH₂ | |
| CH₃ | 5-Cl | H | H | O | O | OCH₃ | CH₃ | CH | 179–181 |
| CH₃ | 5-Cl | H | H | O | O | CH₃ | CH₃ | CH | 204–205 |
| CH₃ | 5-Cl | H | H | O | O | OCH₃ | OCH₃ | N | 180–186 |
| CH₃ | 5-Cl | H | H | O | O | OCH₃ | CH₃ | N | 184–187 |
| CH₃ | 5-Cl | H | H | O | O | H | CH₃ | CCl | 210–211 |
| CH₃ | 5-CH₃ | H | H | O | O | OCH₃ | OCH₃ | CH | 171–174 |
| CH₃ | 5-CH₃ | H | H | O | O | OCH₃ | CH₃ | CH | 181–188 |
| CH₃ | 5-CH₃ | H | H | O | O | CH₃ | CH₃ | CH | 180–183 |
| CH₃ | 5-CH₃ | H | H | O | O | OCH₃ | CH₃ | N | 159–161 |
| CH₃ | 5-CH₃ | H | H | O | O | OCH₃ | OCH₃ | N | 178–181 |
| CH₃ | 5-CH₃ | H | H | O | O | CH₃ | CH₃ | N | |
| CH₃ | 5-CH₃ | H | CH₃ | O | O | OCH₃ | OCH₃ | N | 133–136 |
| CH₃ | 5-CH₂CH₃ | H | H | O | O | OCH₃ | CH₃ | CH | |
|  | H | H | H | O | O | OCH₃ | OCH₃ | CH | 221–223 |
| 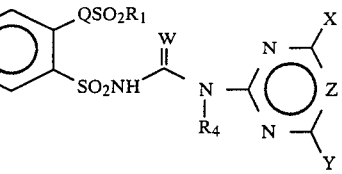 | H | H | H | O | O | CH₃ | CH₃ | CH | 182–186 |
| 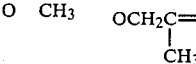 | H | H | H | O | O | OCH₃ | CH₃ | N | 184–186 |
| 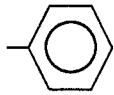 | H | H | H | O | O | OCH₃ | OCH₃ | N | 169–172 |

TABLE I-continued $$\underset{R_3}{\underset{R_2}{\bigcirc}}\overset{QSO_2R_1}{\underset{SO_2NH-\overset{W}{C}-\underset{R_4}{N}}{}}\overset{X}{\underset{Y}{\underset{N}{\bigcirc}}}Z$$

| $R_1$ | $R_2$ | $R_3$ | $R_4$ | Q | W | Y | X | Z | m.p. (°C.) |
|---|---|---|---|---|---|---|---|---|---|
| ⬡ (phenyl) | H | H | H | O | O | $CH_3$ | $CH_3$ | N | |
| ⬡ (phenyl) | H | H | H | O | O | H | $CH_3$ | CCl | 193–195 |
| ⬡ (phenyl) | H | H | $CH_3$ | O | O | $OCH_3$ | $OCH_3$ | N | 143–145 |
| $CH_3$ | H | H | $OCH_3$ | O | O | $OCH_3$ | $OCH_3$ | CH | |
| $-CH_2-\underset{Cl}{CH}-\underset{Cl}{CHCH_3}$ | H | H | H | O | O | $OCH_3$ | $OCH_3$ | CH | |
| $CF_3$ | H | H | H | O | O | $OCH_3$ | $CH_3$ | CH | 135–140(d) |
| $CF_3$ | H | H | H | O | O | $CH_3$ | $CH_3$ | CH | 190–193(d) |
| $CF_3$ | H | H | H | O | O | $OCH_3$ | $OCH_3$ | N | |
| $CF_3$ | H | H | H | O | O | $OCH_3$ | $CH_3$ | N | |
| $CF_3$ | H | H | H | O | O | $CH_3$ | $CH_3$ | N | 200 (d) |
| $CF_3$ | H | H | $CH_3$ | O | O | $OCH_3$ | $OCH_3$ | N | 144–148(d) |
| $CF_3$ | H | H | H | $\underset{CH_3}{N}$ | O | $OCH_3$ | $OCH_3$ | CH | 195–197 |
| $CF_3$ | H | H | H | $\underset{CH_3}{N}$ | O | $OCH_3$ | $CH_3$ | CH | 199–200 |
| $CF_3$ | H | H | H | $\underset{CH_3}{N}$ | O | $CH_3$ | $CH_3$ | CH | 221–224 |
| $CF_3$ | H | H | H | $\underset{CH_3}{N}$ | O | $OCH_3$ | $OCH_3$ | N | 151–154 |
| $CF_3$ | H | H | H | $\underset{CH_3}{N}$ | O | $OCH_3$ | $CH_3$ | N | 180–182 |
| $CF_3$ | H | H | H | $\underset{CH_3}{N}$ | O | $CH_3$ | $CH_3$ | N | 200–201 |
| $CF_3$ | H | H | $CH_3$ | $\underset{CH_3}{N}$ | O | $OCH_3$ | $OCH_3$ | N | |
| $CH_2CH_3$ | H | H | H | O | O | Cl | $OCH_3$ | CH | |
| $CH_2CH_2CH_3$ | H | H | H | O | O | Cl | $OCH_3$ | CH | |
| $CH_3$ | H | H | H | O | O | $OCH_3$ | $N(CH_3)_2$ | CH | |
| $CH_2CH_3$ | H | H | H | O | O | $OCH_3$ | $N(CH_3)_2$ | N | |
| $CH_2CH_2CH_3$ | H | H | H | O | O | $OCH_3$ | $N(CH_3)_2$ | CH | |
| $CH_2CH_3$ | H | H | H | O | O | Cl | $N(CH_3)_2$ | CH | |
| $CH_2CH_2CH_3$ | H | H | H | O | O | Cl | $N(CH_3)_2$ | CH | |
| $CH_3$ | H | H | H | $\underset{CH_3}{-N-}$ | O | Cl | $OCH_3$ | CH | |

TABLE I-continued

| R₁ | R₂ | R₃ | R₄ | Q | W | Y | X | Z | m.p. (°C.) |
|---|---|---|---|---|---|---|---|---|---|
| CF₃ | H | H | H | —N(CH₃)— | O | Cl | OCH₃ | CH | |
| CH₃ | H | H | H | —N(CH₃)— | O | OCH₃ | N(CH₃)₂ | CH | |
| CF₃ | H | H | H | —N(CH₃)— | O | OCH₃ | N(CH₃)₂ | N | |
| CH₃ | H | H | H | —N(CH₃)— | O | Cl | N(CH₃)₂ | CH | |
| CF₃ | H | H | H | —N(CH₃)— | O | Cl | N(CH₃)₂ | CH | |
| CH₃ | H | H | H | —N(CH₃)— | O | CH₃ | CH₃ | N | 212–213 |
| CH₃ | H | H | H | —N(CH₃)— | O | OCH₃ | OCH₃ | N | 224–227 |
| CH₃ | 5-CF₃ | H | H | O | O | Cl | OCH₃ | CH | |
| CH₃ | 5-CF₃ | H | H | O | O | CH₃ | OCH₃ | CH | |
| CH₃ | 5-CF₃ | H | H | O | O | CH₃ | CH₃ | CH | |
| CH₃ | 5-CF₃ | H | H | O | O | CH₃O | CH₃O | N | |
| CH₃ | 5-CF₃ | H | H | O | O | CH₃ | CH₃ | N | |
| CH₃ | 5-CF₃ | H | H | O | O | CH₃ | OCH₃ | N | |
| CH₃ | 5-CF₃ | H | H | O | O | OCH₃ | N(CH₃)₂ | N | |
| CH₃CH₂ | 5-CF₃ | H | H | O | O | Cl | OCH₃ | CH | |
| CH₃CH₂ | 5-CF₃ | H | H | O | O | CH₃O | CH₃O | CH | |
| CH₃CH₂ | 5-CF₃ | H | H | O | O | CH₃ | CH₃ | CH | |
| CH₃CH₂ | 5-CF₃ | H | H | O | O | CH₃ | OCH₃ | CH | |
| CH₃CH₂ | 5-CF₃ | H | H | O | O | CH₃O | CH₃O | N | |
| CH₃CH₂ | 5-CF₃ | H | H | O | O | CH₃ | CH₃O | N | |
| CH₃CH₂ | 5-CF₃ | H | H | O | O | CH₃ | CH₃ | N | |
| CH₃CH₂ | 5-CF₃ | H | H | O | O | CH₃O | N(CH₃)₂ | N | |
| CH₃ | 5-CF₃ | H | H | —N(CH₃)— | O | Cl | OCH₃ | CH | |
| CH₃ | 5-CF₃ | H | H | —N(CH₃)— | O | CH₃O | CH₃O | CH | |
| CH₃ | 5-CF₃ | H | H | —N(CH₃)— | O | CH₃ | CH₃ | CH | |
| CH₃ | 5-CF₃ | H | H | —N(CH₃)— | O | CH₃ | CH₃O | CH | |
| CH₃ | 5-CF₃ | H | H | —N(CH₃)— | O | CH₃ | CH₃ | N | |
| CH₃ | 5-CF₃ | H | H | —N(CH₃)— | O | CH₃O | CH₃O | N | |

TABLE I-continued

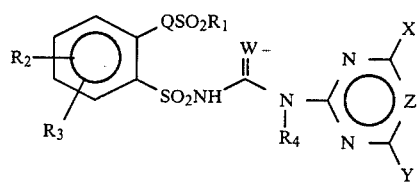

| R₁ | R₂ | R₃ | R₄ | Q | W | Y | X | Z | m.p. (°C.) |
|---|---|---|---|---|---|---|---|---|---|
| CH₃ | 5-CF₃ | H | H | —N(CH₃)— | O | CH₃ | CH₃O | N | |
| CH₃ | 5-CF₃ | H | H | —N(CH₃)— | O | CH₃O | N(CH₃)₂ | N | |
| CH₃ | 5-Cl | H | H | —N(CH₃)— | O | CH₃ | CH₃ | CH | |
| CH₃ | 5-Cl | H | H | —N(CH₃)— | O | CH₃O | CH₃O | CH | |
| CH₃ | 5-Cl | H | H | —N(CH₃)— | O | CH₃O | CH₃ | CH | |
| CH₃ | 5-Cl₃ | H | H | —N(CH₃)— | O | Cl | CH₃O | CH | |
| CH₃ | 5-Cl | H | H | —N(CH₃)— | O | CH₃ | CH₃ | N | |
| CH₃ | 5-Cl | H | H | —N(CH₃)— | O | CH₃O | CH₃O | N | |
| CH₃ | 5-Cl | H | H | —N(CH₃)— | O | CH₃O | CH₃ | N | |
| CH₃ | 5-Cl | H | H | —N(CH₃)— | O | CH₃O | N(CH₃)₂ | N | |

TABLE II

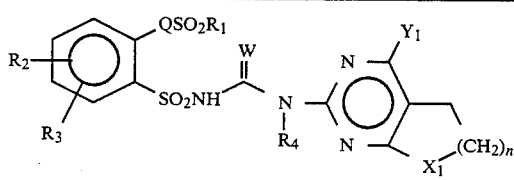

| R₁ | R₂ | R₃ | R₄ | Q | W | X₁ | Y₁ | n | m.p. (°C.) |
|---|---|---|---|---|---|---|---|---|---|
| CH₃ | H | H | H | O | O | O | H | 1 | |
| CH₃ | H | H | H | O | O | O | CH₃ | 1 | |
| CH₃ | H | H | H | O | O | O | OCH₃ | 1 | |
| CH₃ | H | H | H | O | O | O | H | 2 | |
| CH₃ | H | H | H | O | O | O | CH₃ | 2 | |
| CH₃ | H | H | H | O | O | O | OCH₃ | 2 | |
| CH₃ | H | H | H | —N(CH₃)— | O | O | OCH₃ | 2 | |
| CH₃ | 5-Cl | H | H | O | O | O | CH₃ | 1 | |
| CH₃ | 5-Cl | H | H | O | O | O | OCH₃ | 1 | |
| CH₃ | 5-Cl | H | H | O | O | CH₂ | CH₃ | 1 | |
| CH₃ | 5-Cl | H | H | O | O | CH₂ | OCH₃ | 1 | |

TABLE II-continued

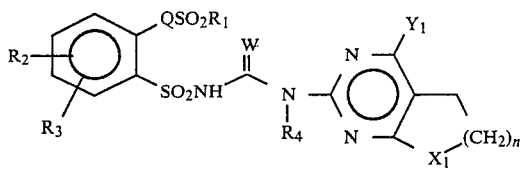

| R₁ | R₂ | R₃ | R₄ | Q | W | X₁ | Y₁ | n | m.p. (°C.) |
|---|---|---|---|---|---|---|---|---|---|
| CH₃ | 5-Cl | H | H | O | O | O | CH₃ | 2 | |
| CH₃ | 5-Cl | H | H | O | O | O | OCH₃ | 2 | |
| —(CH₂)₃CH₃ | H | H | H | O | O | O | OCH₃ | 1 | |
| (CH₂)₂CH₂Cl | H | H | H | O | O | O | OCH₃ | 1 | |
| phenyl | H | H | H | O | O | O | OCH₃ | 1 | |
| 2-chlorophenyl | H | H | H | O | O | O | OCH₃ | 1 | |
| 2-nitrophenyl | H | H | H | O | O | O | OCH₃ | 1 | |
| (CH₂)₂CH₃ | H | H | H | O | O | O | OCH₃ | 1 | |
| CH₂CH₂Cl | H | H | H | O | O | O | OCH₃ | 1 | |
| CH₂CH₂Cl | H | H | H | O | O | O | CH₃ | 1 | |
| CH₂CH₂Cl | H | H | H | O | O | O | OCH₃ | 2 | |
| CH₃ | 5-F | H | H | O | O | O | OCH₃ | 1 | |
| CH₃ | 5-Cl | 4-Cl | H | O | O | O | OCH₃ | 1 | |
| CH₃ | 6-CH₃ | H | H | O | O | O | OCH₃ | 1 | |
| CH₃ | H | H | H | —N(CH₃)— | O | O | OCH₃ | 2 | |
| CH₃ | H | H | H | —N(CH₃)— | O | O | CH₃ | 1 | |
| CH₃ | H | H | H | O | S | O | OCH₃ | 1 | |
| CH₃ | H | H | H | O | S | O | CH₃ | 1 | |
| CH₃ | H | H | CH₃ | O | O | O | CH₃ | 1 | |
| CH₃ | H | H | CH₃ | O | O | CH₂ | CH₃ | 1 | |
| CF₃ | H | H | H | O | O | O | CH₃ | 1 | |
| —CH₂CH₂OCH₃ | H | H | H | O | O | O | CH₃ | 1 | |
| CH₃ | H | H | OCH₃ | O | O | O | CH₃ | 1 | |
| CH₃ | H | H | H | O | O | CH₂ | OCH₃ | 2 | |
| CH₃ | H | H | H | O | O | O | Cl | 1 | |
| CH₃ | H | H | H | O | O | O | Cl | 2 | |

TABLE III

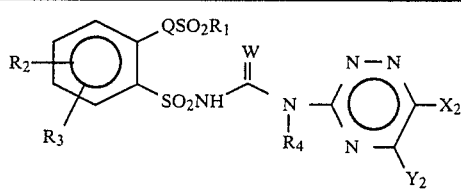

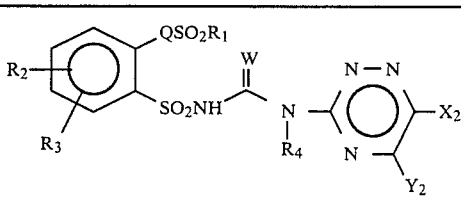

| R₁ | R₂ | R₃ | R₄ | Q | W | X₂ | Y₂ | m.p. (°C.) | R₁ | R₂ | R₃ | R₄ | Q | W | X₂ | Y₂ | m.p. (°C.) |
|---|---|---|---|---|---|---|---|---|---|---|---|---|---|---|---|---|---|
| CH₃ | H | H | H | O | O | OCH₃ | OCH₃ | | CH₃ | H | H | CH₃ | O | O | OCH₃ | OCH₃ | |
| CH₃ | H | H | H | O | O | OCH₃ | CH₃ | | CH₃ | H | H | H | O | O | CH₃ | CH₃ | |
| CH₃ | H | H | H | O | S | OCH₃ | OCH₃ | | CH₃ | H | H | CH₃ | O | O | CH₃ | CH₃ | |

TABLE III-continued $$R_2 - \text{Ar}(QSO_2R_1)(SO_2NH\overset{W}{\underset{\|}{C}}\underset{R_4}{N} - \underset{N}{\overset{N-N}{\diagup}} - X_2, Y_2)$$ with $R_3$

| $R_1$ | $R_2$ | $R_3$ | $R_4$ | Q | W | $X_2$ | $Y_2$ | m.p. (°C.) |
|---|---|---|---|---|---|---|---|---|
| $CH_3$ | H | H | H | N–$CH_3$ | O | $OCH_3$ | $OCH_3$ | |
| $CF_3$ | H | H | H | O | O | $OCH_3$ | $OCH_3$ | |
| $CH_2CH_2OCH_3$ | H | H | H | O | O | $OCH_3$ | $OCH_3$ | |
| –⌬ (phenyl) | H | H | H | O | O | $OCH_3$ | $OCH_3$ | |
| $CH_3$ | 5-Cl | H | H | O | O | $OCH_3$ | $OCH_3$ | |
| $CH_3$ | 5-$CH_3$ | H | H | O | O | $OCH_3$ | $OCH_3$ | |
| $CH_3$ | H | H | $OCH_3$ | O | O | $OCH_3$ | $OCH_3$ | |

TABLE IV $$R_2 - \text{Ar}(QSO_2R_1)(SO_2NH\overset{W}{\underset{\|}{C}}\underset{R_4}{N} - \underset{N}{\overset{X_2}{\diagup}}, Y_2)$$ with $R_3$

| $R_1$ | $R_2$ | $R_3$ | $R_4$ | Q | W | $X_2$ | $Y_2$ | m.p. (°C.) |
|---|---|---|---|---|---|---|---|---|
| $CH_3$ | H | H | H | O | O | $OCH_3$ | $OCH_3$ | |
| $CH_3$ | H | H | H | O | O | $OCH_3$ | $CH_3$ | |
| $CH_3$ | H | H | H | O | S | $OCH_3$ | $OCH_3$ | |
| $CH_3$ | H | H | $CH_3$ | O | O | $OCH_3$ | $OCH_3$ | |
| $CH_3$ | H | H | H | O | O | $CH_3$ | $CH_3$ | |
| $CH_3$ | H | H | $CH_3$ | O | O | $CH_3$ | $CH_3$ | |
| $CH_3$ | H | H | H | N–$CH_3$ | O | $OCH_3$ | $OCH_3$ | |
| $CF_3$ | H | H | H | O | O | $OCH_3$ | $OCH_3$ | |
| $CH_2CH_2OCH_3$ | H | H | H | O | O | $OCH_3$ | $OCH_3$ | |
| –⌬ (phenyl) | H | H | H | O | O | $OCH_3$ | $OCH_3$ | |
| $CH_3$ | 5-Cl | H | H | O | O | $OCH_3$ | $OCH_3$ | |
| $CH_3$ | 5-$CH_3$ | H | H | O | O | $OCH_3$ | $OCH_3$ | |
| $CH_3$ | H | H | $OCH_3$ | O | O | $OCH_3$ | $OCH_3$ | |

TABLE V $$R_2 - \text{Ar}(QSO_2R_1)(SO_2NCW)$$ with $R_3$

| $R_1$ | $R_2$ | $R_3$ | W | IR (cm$^{-1}$) |
|---|---|---|---|---|
| $CH_3$ | H | H | O | 2210 |
| n-Bu | H | H | O | 2220 |
| $CH_3$ | 5-Cl | H | O | 2210 |
| $C_2H_5$ | H | H | O | 2210 |
| n-Pr | H | H | O | 2210 |
| $CH_3$ | 5-$CH_3$ | H | O | 2230 |
| $CH_3$ | 3-Cl | H | O | 2220 |
| $CF_3$ | H | H | O | 2220 |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VI

| | Active Ingredient | Weight Percent* Diluent(s) | Surfactants(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing. Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

Wettable powder

N-[(4,6-dimethoxypyrimidin-2-yl)aminocarbonyl]-2-hydroxybenzenesulfonamide, methanesulfonate—80%
  sodium alkylnaphthalenesulfonate—2%
  sodium ligninsulfonate—2%
  synthetic amorphous silica—3%
  kaolinite—13%

The ingredients are blended, hammer-milled until all the solids are essentially under 50 microns and then reblended.

EXAMPLE 10

Wettable Powder 2-hydroxy-N-[(4-methoxy-6-methylpyrimidin-2-yl)aminocarbonyl]benzenesulfonamide, methanesulfonate—50%
  sodium alkylnaphthalenesulfonate—2%
  low viscosity methyl cellulose—2%
  diatomaceous earth—46%

The ingredients are blended, coarsely hammer-milled and then air-milled to produce particles essentially all below 10 microns in diameter. The product is reblended before packaging.

EXAMPLE 11

Granule

Wettable Powder of Example 10—5%
  attapulgite granules (U.S.S. 20–40 mesh; 0.84–0.42 mm)—95%

A slurry of wettable powder containing ≈25% solids is sprayed on the surface of attapulgite granules in a double-cone blender. The granules are dried and packaged.

EXAMPLE 12

Extruded Pellet 2-hydroxy-N-[(4-methoxy-6-methyl-1,3,5-triazin-2-yl)-aminocarbonyl]benzenesulfonamide, methanesulfonate—25%
  anhydrous sodium sulfate—10%
  crude calcium ligninsulfonate—5%
  sodium alkylnaphthalenesulfonate—1%
  calcium/magnesium bentonite—59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Oil Suspension

N-[(4,6-dimethylpyrimidin-2-yl)aminocarbonyl]-2-hydroxybenzenesulfonamide, methanesulfonate—25%
  polyoxyethylene sorbitol hexaoleate—5%
  highly aliphatic hydrocarbon oil—70%

The ingredients are ground together in a sand mill until the solid particles have been reduced to under about 5 microns. The resulting thick suspension may be applied directly, but preferably after being extended with oils or emulsified in water.

EXAMPLE 14

Wettable Powder

N-[(4,6-dimethoxy-1,3,5-triazin-2-yl)aminocarbonyl]-2-hydroxybenzenesulfonamide, methanesulfonate—20%
  sodium alkylnaphthalenesulfonate—4%
  sodium ligninsulfonate—4%
  low viscosity methyl cellulose—3%
  attapulgite—69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 15

Low Strength Granule

N-[(4,6-dimethoxy-1,3,5-triazin-2-yl)(methyl)aminocarbonyl]-2-hydroxybenzenesulfonamide, methanesulfonate—1%
  N,N-dimethylformamide—9%
  attapulgite granules (U.S.S. 20–40 sieve)—90%

The active ingredient is dissolved in the solvent and the solution is sprayed upon dedusted granules in a double cone blender. After spraying of the solution has been completed, the blender is allowed to run for a short period and then the granules are packaged.

EXAMPLE 16

Aqueous Suspension

N-[(4,6-dimethyl-1,3,5-triazin-2-yl)aminocarbonyl]-2-hydroxybenzenesulfonamide, methanesulfonate—40% polyacrylic acid thickener—0.3%
dodecylphenol polyethylene glycol ether—0.5%
disodium phosphate—1%
monosodium phosphate—0.5%
polyvinyl alcohol—1.0%
water—56.7%

The ingredients are blended and ground together in a sand mill to produce particles essentially all under 5 microns in size.

EXAMPLE 17

Solution

N-[(4,6-dimethylpyrimidin-2-yl)aminocarbonyl]-2-hydroxybenzenesulfonamide, methanesulfonate, sodium salt—5%
water—95%

The salt is added directly to the water with stirring to produce the solution, which may then be packaged for use.

EXAMPLE 18

Low Strength Granule 2-hydroxy-N-[(4-methoxy-6-methylpyrimidin-2-yl)aminocarbonyl]benzenesulfonamide, methanesulfonate—0.1%
attapulgite granules (U.S.S. 20-40 mesh)—99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 19

Granule

N-[(4,6-dimethoxypyrimidin-2-yl)aminocarbonyl]-2-hydroxybenzenesulfonamide, methanesulfonate—80%
wetting agent—1%
crude ligninsulfonate salt (containing 5-20% of the natural sugars)—10%
attapulgite clay—9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 20

High Strength Concentrate

N-[(4,6-dimethoxy-1,3,5-triazin-2-yl)aminocarbonyl]-2-hydroxybenzenesulfonamide, methanesulfonate—99%
silica aerogel—0.5%
synthetic amorphous silica—0.5%

The ingredients are blended and ground in a hammer-mill to produce a material essentially all passing a U.S.S. No. 50 screen (0.3 mm opening). The concentrate may be formulated further if necessary.

EXAMPLE 21

Wettable Powder 2-hydroxy-N-[(4-methoxy-6-methyl-1,3,5-triazin-2-yl)-aminocarbonyl]benzenesulfonamide, methanesulfonate—90%
dioctyl sodium sulfosuccinate—0.1%
synthetic fine silica—9.9%

The ingredients are blended and ground in a hammer-mill to produce particles essentially all below 100 microns. The material is sifted through a U.S.S. No. 50 screen and then packaged.

EXAMPLE 22

Wettable Powder

N-[(4,6-dimethyl-1,3,5-triazin-2-yl)aminocarbonyl]-2-hydroxybenzenesulfonamide, methanesulfonate—40%
sodium ligninsulfonate—20%
montmorillonite clay—40%

The ingredients are thoroughly blended, coarsely hammer-milled and then air-milled to produce particles essentially all below 10 microns in size. The material is reblended and then packaged.

EXAMPLE 23

Oil Suspension 2-hydroxy-N-[(4-methoxy-6-methyl-1,3,5-triazin-2-yl)-aminocarbonyl]benzenesulfonamide, 1-propanesulfonate—35%
blend of polyalcohol carboxylic esters and oil soluble petroleum sulfonates—6%
xylene—59%

The ingredients are combined and ground together in a sand mill to produce particles essentially all below 5 microns. The product can be used directly, extended with oils, or emulsified in water.

EXAMPLE 24

Dust

N-[(4,6-dimethoxypyrimidin-2-yl)aminocarbonyl]-2-hydroxybenzenesulfonamide, 1-propanesulfonate—10%
attapulgite—10%
Pyrophyllite—80%

The active ingredient is blended with attapulgite and then passed through a hammer-mill to produce substantially all below 200 microns. The ground concentrate is then blended with powdered pyrophyllite until homogeneous.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, compounds of this invention may also be used to modify plant growth beneficially, and also to selectively control weeds in crops such as wheat, barley, rice, corn and soybeans.

The precise amount of the compounds of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used at levels of about 0.001 to 20 kg/ha with a preferred range of 0.01 to 10 kg/ha. In general, the higher rates of application from within this range will be selected for adverse conditions or where extended persistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosponomethyl)glycine(glyphosate); 3-cyclohexyl-1-methyl-6-dimethylamino-s-triazine-2,4(1H,3H)-dione(hexazinone); N,N-dimethyl-2,2-diphenylacetamide(diphenamid); 2,4-dichlorophenoxyacetic acid (2,4-D) (and closely related compounds); 4-chloro-2-butynyl-3-chlorophenylcarbamate(barban); S-(2,3-dichloroallyl)-diisopropylthiocarbamate(diallate); S-(2,3,3-trichloroallyl)-diisopropylthiocarbamate(triallate); 1,2-dimethyl-3,5-diphenyl-1H-pyrazolium methyl sulfate (difenzoquat methyl sulfate); methyl 2-[4-(2,4-dichlorophenoxy)-phenoxy]-propanoate(diclofop methyl); 4-amino-6-tert-butyl-3-(methylthio)-1,2,4-triazin-5(4H)-one (metribuzin); 3-(3,4-dichlorophenyl)-1-methoxy-1-methylurea (linuron); 3-isopropyl-1H-2,1,3-benzothiodiazin-4(3H)-one-2,2-dioxide(bentazon); α,α,α-trifluoro-2,6-dinitro-N,N-dipropyl-p-toluidine(trifluralin); 1,1'-dimethyl-4,4'-bipyridinium ion (paraquat); monosodium methanearsonate (MSMA); 2-chloro-2',6'-diethyl(methoxymethyl)acetanilide(alachlor); 1,1-dimethyl-3-(α,α,α-trifluoro-m-tolyl)-urea(fluometuron); 5-[2-chloro-4-(trifluoromethyl)-phenoxy]-2-nitrobenzoic acid, methyl ester(acifluorofen-methyl); 3-amino-2,5-dichlorobenzoic acid (chloramben); N-(2-chloroethyl)-2,6-dinitro-N-propyl-4-trifluoromethyl)aniline(fluchloralin); 3,4-dinitro-N,N-dipropylsulfanilamide(oryzalin); N-(1-ethylpropyl)-3,4-dimethyl-2,6-dinitrobenzeneamine(pendimethalin); N-(cyclopropylmethyl)-α,α,α-trifluoro-2,6-dinitro-N-propyl-p-toluidine(profluralin); 2-chloro-N-(2ethyl-6-methylphenyl)-N-(2-methoxy-1-methylethyl)acetamide(metolachlor); 4-(6-chloroquinoxalinyl-2-oxy)phenoxypropionate $C_1$-$C_5$ alkyl esters, such as methyl ester, butyl ester, ethyl ester, pentyl ester; ethoxyethoxyethyl 4-(6-chloroquinoxalinyl-2-oxy)phenoxypropionate; butyl 2-[4-[5-(trifluoromethyl)-2-pyridinyloxy]phenoxy]-propanoate(fluazifop-butyl); N-[2,4-dimethyl-5-]](trifluoromethyl)sulfonyl]amino]phenyl]acetamide(mefluidide); 2-[1-(ethoxyimino)butyl]-5-[2-(ethylthio)propyl]-3-hydroxy-2-cyclohexene-1-one (sethoxydim); 2-s-butyl-4,6-dinitrophenol(dinoseb); 4-(2,4-dichlorophenoxy)butyric acid (2,4-DB); propargyl 2-[4-(3,5-dichloropyridin-2-yloxy)phenoxy]propanoate (CGA 82725); methyl 2-[4-(3-chloro-5-trifluoromethylpyridin-2-yloxy)phenoxy]propanoate (DOWCO 453); 5-(2-chloro-4-trifluoromethylphenoxy)-N-methylsulfonyl-2-nitrobenzamide(fomesafen); 2-[1-(2,5-dimethylphenyl)ethylsulfonyl]pyridine-N-oxide (UBI-S-734); and 2-chloro-1-(3-ethoxy-4-nitrophenoxy)-4-(trifluoromethyl)benzene(oxyfluorfen).

The activity of these compounds was discovered in greenhouse tests. The tests are described and data resulting from them are shown below.

Test A

Seeds of crabgrass (*Digitaria* spp.), barnyard-grass (*Echinochloa crusgalli*), wild oats (*Avena fatua*), cassia (*Cassia tora*), morningglory (*Ipomoea* sp.), cocklebur (*Xanthium* spp.), sorghum, corn, soybean, rice, wheat and nutsedge tubers (*Cyperus rotundus*) were planted in a growth medium and treated pre-emergence with the chemicals dissolved in a non-phytotoxic solvent solution of the compounds of Table A. At the same time, cotton having five leaves (including cotyledonary ones), bush beans with the third trifoliate leaf expanding, crabgrass and barnyardgrass with two leaves, wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three–five leaves were sprayed with a non-phytotoxic solvent solution of the compounds of Table A. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0=no effect
10=maximum effect
C=chlorosis or necrosis
D=defoliation
E=emergence inhibition
G=growth retardation
H=formative effects
U=unusual pigmentation
6Y=abscised buds or flowers
P=terminal bud kill
B=burn
X=axillary stimulation

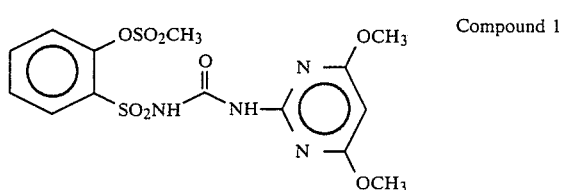

Compound 1

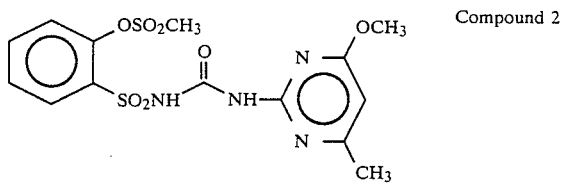

Compound 2

-continued
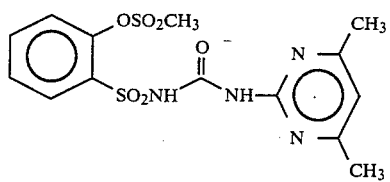 Compound 3
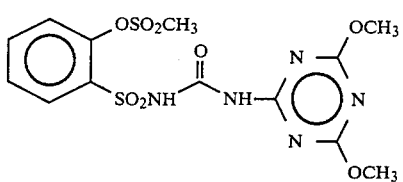 Compound 4
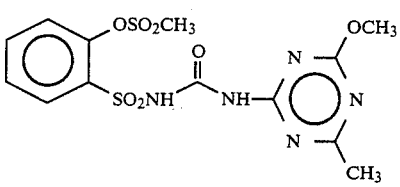 Compound 5
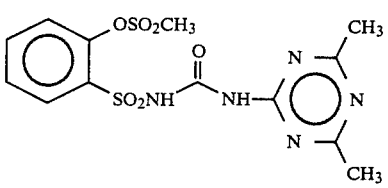 Compound 6
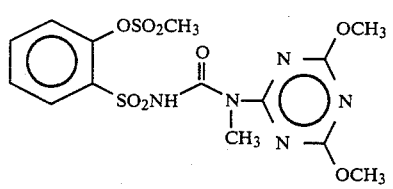 Compound 7
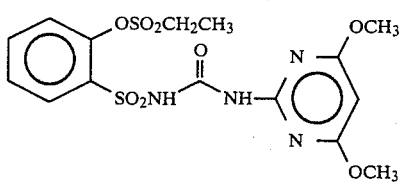 Compound 8
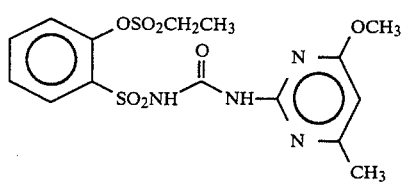 Compound 9
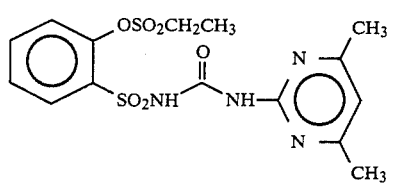 Compound 10
-continued
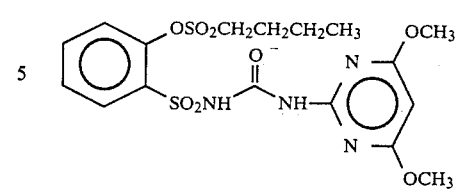 Compound 11
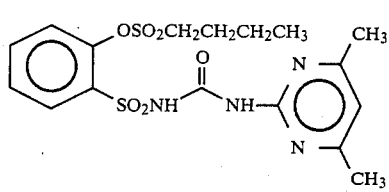 Compound 12
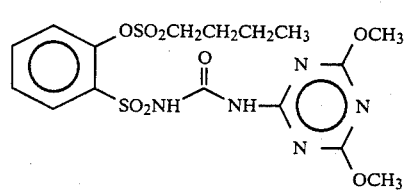 Compound 13
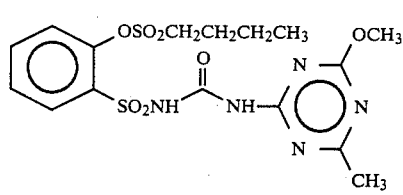 Compound 14
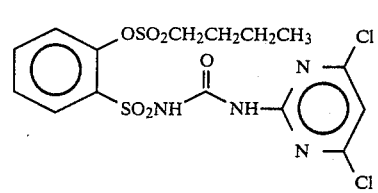 Compound 15
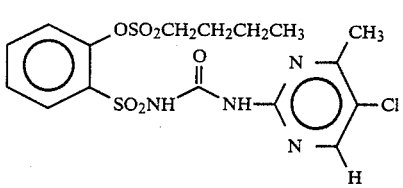 Compound 16
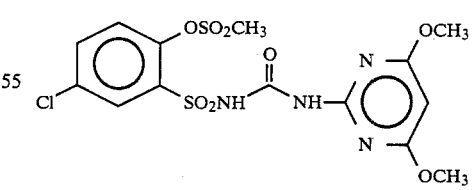 Compound 17
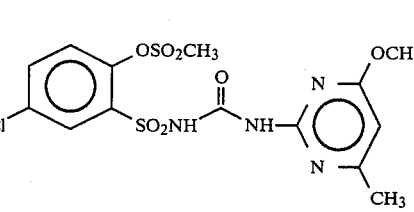 Compound 18

-continued
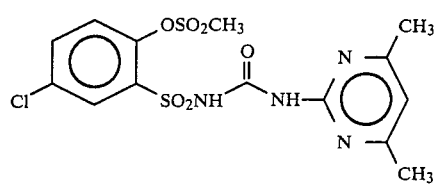
Compound 19
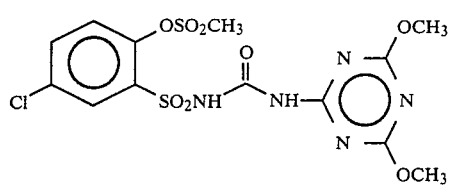
Compound 20
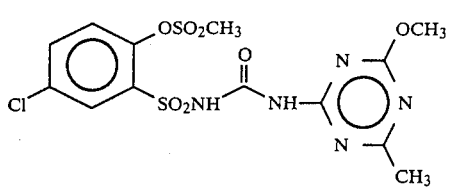
Compound 21
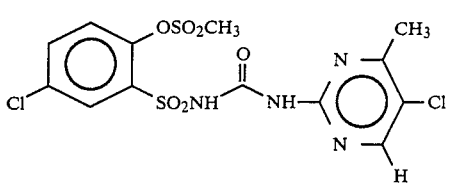
Compound 22
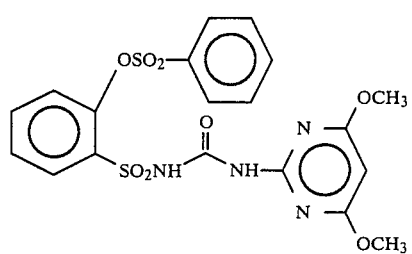
Compound 23
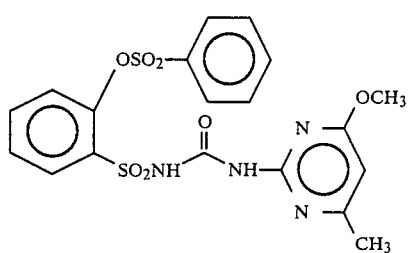
Compound 24
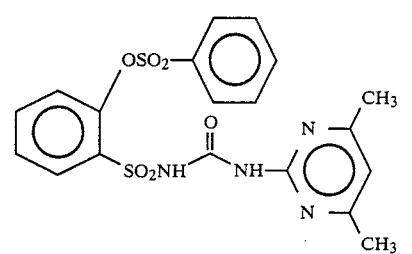
Compound 25
-continued
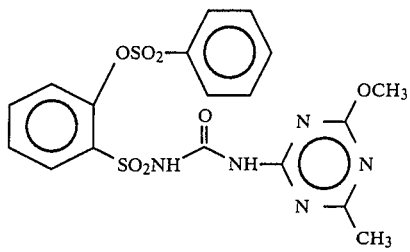
Compound 26
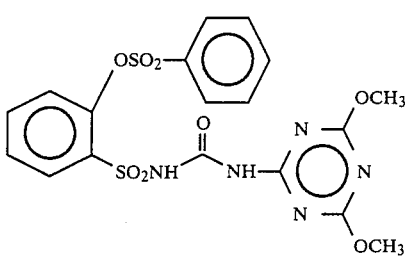
Compound 27
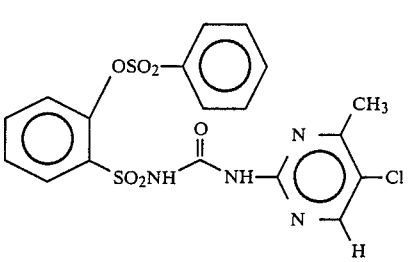
Compound 28
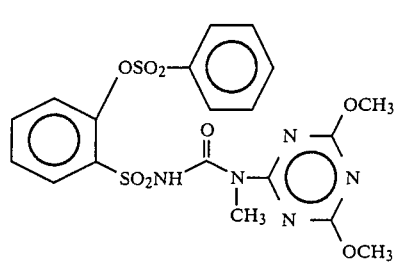
Compound 29
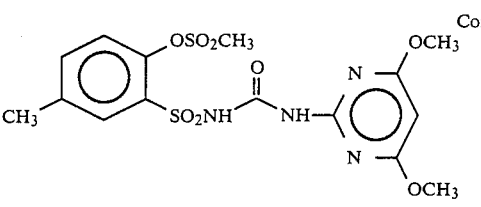
Compound 30
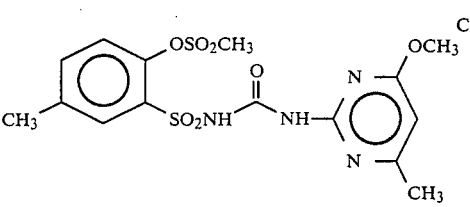
Compound 31
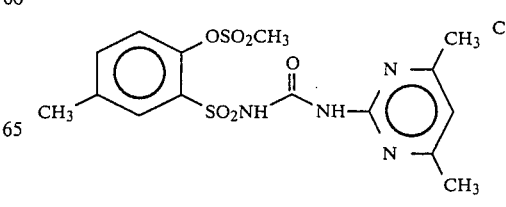
Compound 32

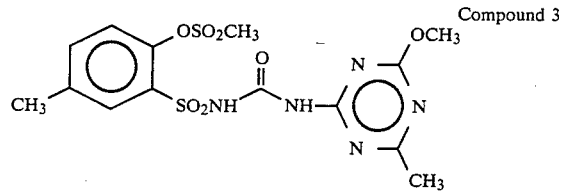 Compound 33
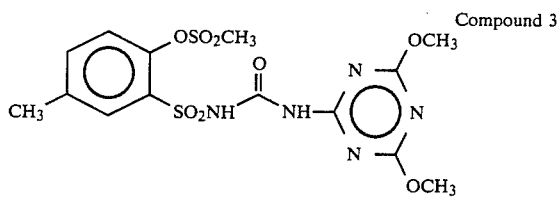 Compound 34
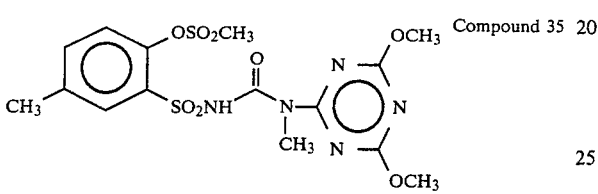 Compound 35
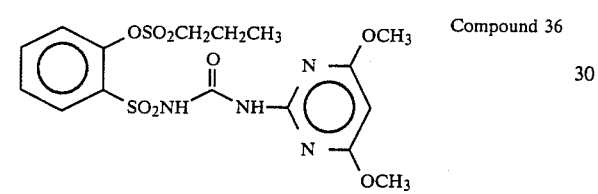 Compound 36
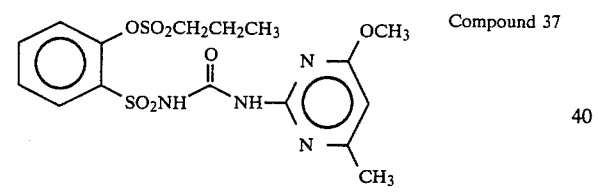 Compound 37
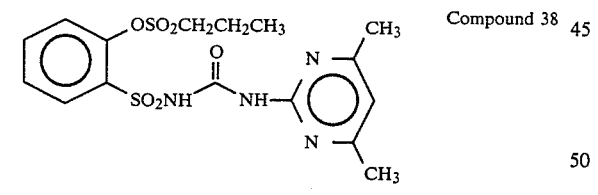 Compound 38
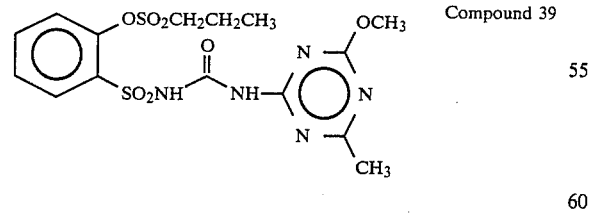 Compound 39
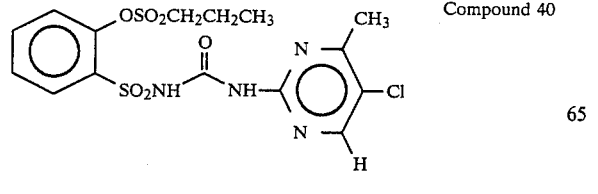 Compound 40
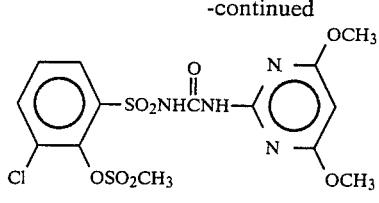 Compound 41
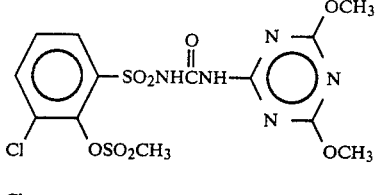 Compound 42
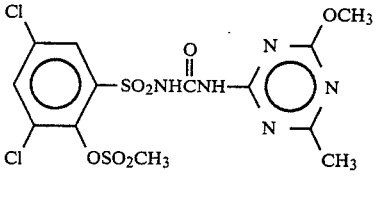 Compound 43
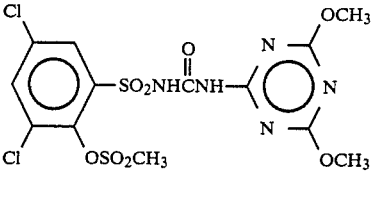 Compound 44
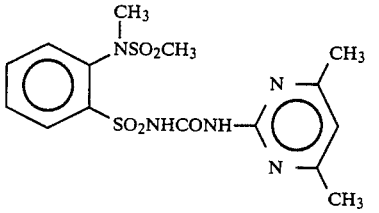 Compound 45
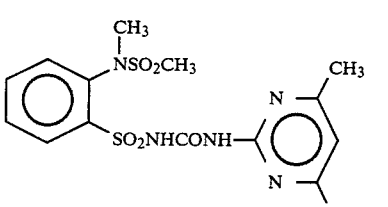 Compound 46
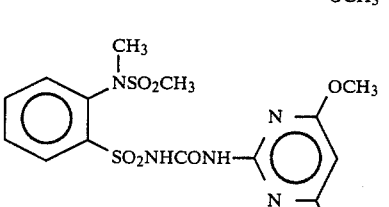 Compound 47
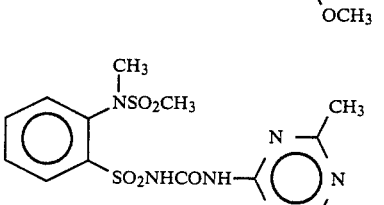 Compound 48

-continued

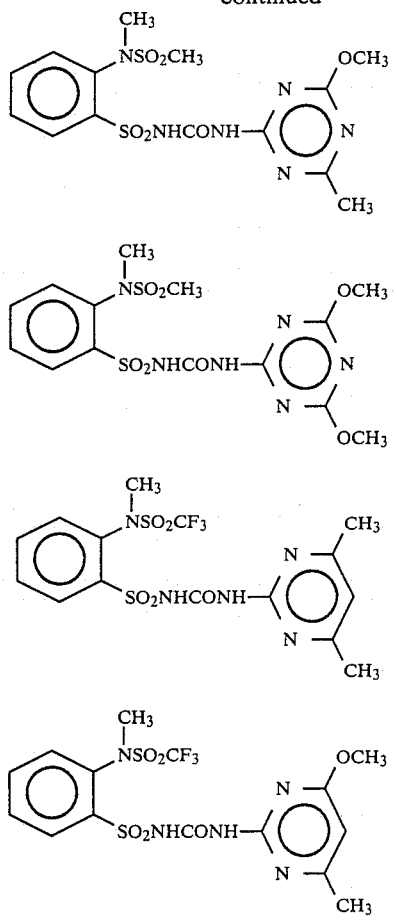

Compound 49

Compound 50

Compound 51

Compound 52

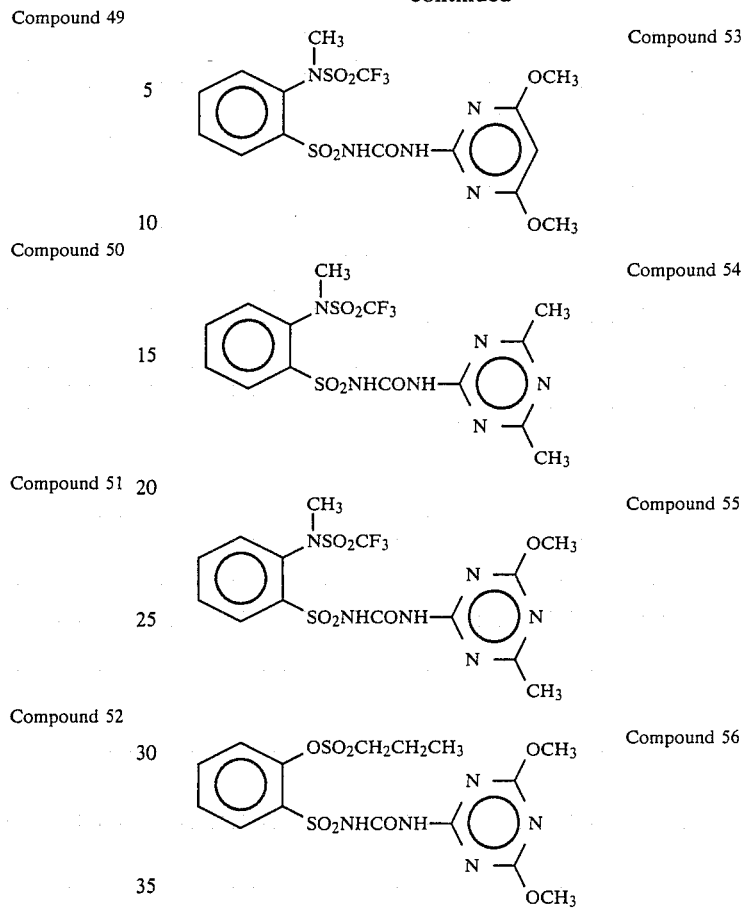

Compound 53

Compound 54

Compound 55

Compound 56

TABLE A

| Rate kg/ha | Cmpd. 1<br>0.1 | Cmpd. 2<br>0.1 | Cmpd. 3<br>0.1 | Cmpd. 4<br>0.1 | Cmpd. 5<br>0.1 | Cmpd. 6<br>0.1 | Cmpd. 7<br>0.1 | Cmpd. 8<br>0.05 | Cmpd. 9<br>0.05 | Cmpd. 10<br>0.05 |
|---|---|---|---|---|---|---|---|---|---|---|
| | | | | POST-EMERGENCE | | | | | | |
| Bush bean | 9C | 9C | 9C | 9C | 9C | 9C | 1C,2G | 10G,9C | 9G,3H,6C | 7G,3H,7C |
| Cotton | 10C | 9C | 10C | 9C | 9C | 9C | 9C | 10G,9C | 10G,8C | 10G,8C |
| Sorghum | 9C | 10C | 9C | 2C,9H | 2C,9H | 6C,9G | 1C,3G | 10G,4C | 10C | 10G,9C |
| Corn | 5C,9G | 9C | 9C | 4U,9G | 6C,9G | 6C,9H | 3C,9H | 7G,5H | 10G,8C | 10G,3H |
| Soybean | 9C | 9C | 9C | 9C | 9C | 9C | 9C | 10G,7C | 10G,8C | 7G,7C |
| Wheat | 1C,2G | 5C,9G | 5C,9G | 0 | 0 | 1C | 0 | 0 | 3C,2C | 3G,2C |
| Wild Oats | 2C,9G | 4C,9G | 5C,9G | 0 | 1C,4G | 3C,9G | 0 | 0 | 9G,3C | 10G,6C |
| Rice | 9C | 9C | 9C | 9C | 9C | 9C | 6G | 8G,3C | 10C | 10C |
| Barnyardgrass | 10C | 10C | 10C | 4C,9H | 5C,9H | 9C | 0 | 10G,6C | 10C | 10G,9C |
| Crabgrass | 9C | 9C | 9C | 4C,9G | 2C,9G | 9C | 3G | 0 | 8G,3C | 0 |
| Morningglory | 10C | 10C | 10C | 10C | 10C | 10C | 9C | 10G,9C | 7G,9C | 10G,5C |
| Cocklebur | 10C | 10C | 9C | 10C | 9C | 9C | 9C | 10G,9C | 10C | 10G,7C |
| Cassia | 9C | 9C | 9C | 9C | 9C | 6C,9G | 5C,9G | 10C | 10G,8C | 10G,8C |
| Nutsedge | 9C | 9C | 9C | 1C,5G | 5G | 1C,5G | 2C,5G | 10G,7C | 10G,6C | 10G,7C |

| Rate kg/ha | Cmpd. 11<br>0.05 | Cmpd. 12<br>0.05 | Cmpd. 13<br>0.05 | Cmpd. 14<br>0.05 | Cmpd. 15<br>0.1 | Cmpd. 16<br>0.1 | Cmpd. 17<br>0.05 | Cmpd. 18<br>0.05 | Cmpd. 19<br>0.05 | Cmpd. 20<br>0.05 |
|---|---|---|---|---|---|---|---|---|---|---|
| | | | | POST-EMERGENCE | | | | | | |
| Bush bean | 2C,2H | 1C,2H | 6C,9G,6Y | 6C,9G,6Y | 0 | 0 | 3C,5G,6Y | 9C,7G | 6C,7G,6Y | 2G |
| Cotton | 3C,2H,6G | 1C | 3C,3H,9G | 3C,3H,9G | 0 | 0 | 7C,6G | 8C,7G | 9C,6G | 5C,4G |
| Sorghum | 0 | 6H | 0 | 0 | 0 | 0 | 3C,4G | 2C,4G | 2C,4G | 4C,5G |
| Corn | 0 | 0 | 0 | 0 | 0 | 0 | 4C,3U,4G | 5C,6G | 0 | 10C |
| Soybean | 2H,6G | 1H | 2H,6G | 2H,5G | 0 | 0 | 6C,7G | 10C | 7C,6G | 4C,5G |
| Wheat | 0 | 0 | 0 | 0 | 0 | 0 | 0 | 0 | 2C,2G | 0 |
| Wild Oats | 0 | 0 | 0 | 0 | 0 | 0 | 2C | 3C,4G | 3G | 4C,5G |
| Rice | 1C | 0 | 0 | 0 | 0 | 0 | 2C,3G | 3C,4G | 3C,5G | 3C,4G |
| Barnyardgrass | 2H | 0 | 0 | 0 | 0 | 0 | 10C | 7C,6G | 2C,3G | 7C,6G |
| Crabgrass | 0 | 0 | 0 | 0 | 0 | 0 | 2C,3G | 0 | 0 | 2C,2G |
| Morningglory | 9C | 1C,5G | 4C,9H | 3C,9H | 0 | 0 | 10C | 5C,4G | 10C | 10C |
| Cocklebur | 3C,9G | 1C | 4C,9H | 2C,8G | 0 | 0 | 8C,7G | 8C,7G | 10C | 10C |
| Cassia | 0 | 0 | 3C | 1C | 0 | 0 | 8C,7G | 3C,4G | 3C,4G | 2C |

TABLE A-continued

| | | | | | | | | | | |
|---|---|---|---|---|---|---|---|---|---|---|
| Nutsedge | 0 | 0 | 0 | 0 | 0 | 0 | 10C | 6C,4G | 5C,4G | 0 |

| Rate kg/ha | Cmpd. 21<br>0.05 | Cmpd. 22<br>0.1 | Cmpd. 30<br>0.05 | Cmpd. 31<br>0.05 | Cmpd. 32<br>0.05 | Cmpd. 33<br>0.05 | Cmpd. 34<br>0.05 | Cmpd. 35<br>0.1 | Cmpd. 36<br>0.05 |
|---|---|---|---|---|---|---|---|---|---|
| | | | | POST-EMERGENCE | | | | | |
| Bush bean | 9C,6G,6Y | 3C,4G,6Y | 3C,9G,6Y | 9C | 9D,9G,6Y | 9D,9G,6Y | 4C,6G,6Y | 2G | 5C,9G,6Y |
| Cotton | 9C,5G | 0 | 5G,9G | 6C,9G | 3H,6C,9G | 6C,9G | 3H,6C,9G | 3C,3H,7G | 9C |
| Sorghum | 6C,5G | 0 | 10C | 2C,9G | 9C | 3C,9G | 1C,6H | 1C,3G | 9C |
| Corn | 7C,6G | 0 | 10C | 7U,9G | 1C,9G | 3U,9G | 1C,5G | 0 | 1C,2G |
| Soybean | 5C,6G | 0 | 2C,9G | 4C,9G | 5C,9G | 3C,9G | 2C,9G | 2C,9G | 2C,8G |
| Wheat | 2C,3G | 0 | 9C | 2C,7G | 9C | 1C,3G | 0 | 0 | 0 |
| Wild Oats | 8C,7G | 0 | 2C,8G | 1C,8G | 9C | 1C,2G | 0 | 0 | 2G |
| Rice | 2C,3G | 0 | 10C | 3C,9G | 9C | 2C,9G | 8G | 0 | 4C,9G |
| Barnyardgrass | 10C | 0 | 10C | 9C | 10C | 10C | 3C,7H | 0 | 3C,9H |
| Crabgrass | 7C,6G | 0 | 6C,9G | 6G | 2C,5G | 1C,3G | 1C,3G | 0 | 2C,4G |
| Morningglory | 10C | 0 | 9C | 10C | 10C | 3C,9G | 9C | 6C,9G | 9C |
| Cocklebur | 10C | 0 | 9C | 10C | 9C | 6C,9G | 6C,9G | 4C,9G | 10C |
| Cassia | 5C,3G | 0 | 9C | 9C | 9C | 3C,7G | 3C,5G | 2C | 5C,9G |
| Nutsedge | 3C,4G | 0 | 9C | 1C,9G | 4C,9G | 2C,7G | 1C,3G | 1C,2G | 9G |

| Rate kg/ha | Cmpd. 37<br>0.05 | Cmpd. 38<br>0.05 | Cmpd. 39<br>0.05 | Cmpd. 40<br>0.4 | Cmpd. 23<br>0.05 | Cmpd. 24<br>0.05 | Cmpd. 25<br>0.05 | Cmpd. 26<br>0.05 | Cmpd. 27<br>0.05 | Cmpd. 28<br>0.4 |
|---|---|---|---|---|---|---|---|---|---|---|
| | | | | POST-EMERGENCE | | | | | | |
| Bush bean | 9C | 4C,9G,6Y | 9C | 0 | 3G | 1H | 0 | 3C,9G,6Y | 1C,2G,6Y | 0 |
| Cotton | 9C | 5C,9G | 9C | 1C | 0 | 0 | 0 | 2C | 1C | 0 |
| Sorghum | 3U | 10C | 1C | 4G | 0 | 2G | 0 | 0 | 3G | 0 |
| Corn | 2C | 2C,4G | 1C | 0 | 0 | 3G | 0 | 2C,3G | 1C | 0 |
| Soybean | 2C | 1H,6G | 1H | 0 | 7G | 1H | 0 | 2H | 2H | 0 |
| Wheat | 0 | 0 | 0 | 0 | 0 | 0 | 0 | 0 | 0 | 0 |
| Wild Oats | 1C | 5G | 2G | 0 | 0 | 0 | 0 | 0 | 0 | 0 |
| Rice | 2C | 7G | 0 | 2G | 0 | 4G | 0 | 0 | 4G | 0 |
| Barnyardgrass | 10C | 3C,7H | 2G | 0 | 0 | 0 | 0 | 0 | 0 | 0 |
| Crabgrass | 3C | 2C,5G | 1C | 5G | 0 | 3G | 0 | 0 | 1C | 0 |
| Morningglory | 9C | 2C,9G | 9C | 3G | 0 | 2G | 0 | 2C,6H | 1C | 3B |
| Cocklebur | 10C | 9C | 10C | 3G | 2G | 1C | 0 | 2C,6G | 3C,6H | 0 |
| Cassia | | 5G | | 0 | | | 0 | | | |
| Nutsedge | 1C | 8G | 2G | 3G | 0 | 0 | 0 | 0 | 1C | 0 |

| Rate kg/ha | Cmpd. 29<br>0.05 | Cmpd. 41<br>0.4 | Cmpd. 42<br>0.4 | Compound 43<br>2  6 | Compound 44<br>2  6 | Cmpd. 45<br>0.05 | Cmpd. 46<br>0.05 | Cmpd. 47<br>0.05 | Cmpd. 48<br>0.05 |
|---|---|---|---|---|---|---|---|---|---|
| | | | | POST-EMERGENCE | | | | | |
| Bush bean | 0 | 9C | 9C | 0  3C | 0  0 | 4C,9G,6Y | 9C | 9C | 4C,8G,6Y |
| Cotton | 0 | 10C | 4C,3H,9G | 0  3C | 0  2C | 6C,9G | 6C,9G | 8C,9G | 3C |
| Sorghum | 0 | 6U,9G | 2C,9G | 0  0 | 0  2C | 2C,9G | 5C,9G | 8U,9G | 2C,9H |
| Corn | 0 | 2U,9H | 5U,9G | 0  0 | 0  0 | 3G | 3C,9H | 5U,9G | 3C,9H |
| Soybean | 0 | 9C | 9C | 0  1C | 0  3G | 1C,8H | 5C,9G | 9C | 2C,6G,5X |
| Wheat | 0 | 2G | 0 | 0  0 | 0  0 | 1C | 1C | 1C | 0 |
| Wild Oats | 0 | 1C,8G | 0 | 0  0 | 0  0 | 2C,8G | 3C,9G | 2C,9G | 2C,7G |
| Rice | 0 | 6C,9G | 6C,9G | 0  0 | 0  0 | 3C,9G | 5C,9G | 5C,9G | 2C,8G,5X |
| Barnyardgrass | 0 | 5C,9H | 1C,6G | 0  1C | 0  0 | 5C,9H | 9C | 6C,9H | 2C,8H |
| Crabgrass | 0 | 2C,6G | 4G | 0  0 | 0  0 | 3C,7H | 4C,9H | 9C | 0 |
| Morningglory | 1C,2G | 6C,9G | 6C,9G | 0  0 | 0  1C,3G | 6C,9G | 9C | 7C,9G | 3C,8H |
| Cocklebur | 0 | 10C | 9C | 0  0 | 0  0 | 5C,9G | 9C | 9C | 1C,4G |
| Cassia | | 9C | 4C,7H | 0  1C | 0  0 | 3C,6H | 5C,9H | 5C,9G | 1C,3G |
| Nutsedge | 0 | 2C,8G | 2C,5G | 0  0 | 0  0 | 5C,9G | 10C | 9C | 3G |

| Rate kg/ha | Cmpd. 49<br>0.05 | Cmpd. 50<br>0.05 | Cmpd. 51<br>0.05 | Cmpd. 52<br>0.05 | Cmpd. 53<br>0.05 | Cmpd. 54<br>0.05 | Cmpd. 55<br>0.05 | Cmpd. 56<br>0.05 |
|---|---|---|---|---|---|---|---|---|
| | | | | POST-EMERGENCE | | | | |
| Bush bean | 9C | 9C | 0 | 3C,3H,6Y | 4C,9G,6Y | 1C | 3C,9G,6Y | 9C |
| Cotton | 6C,9G | 6C,9G | 0 | 2C,2H | 4C,7H | 1C,2G | 2C,6G | 6C,9G |
| Sorghum | 9C | 9C | 0 | 2C,4G | 1C,3G | 0 | 2C,9H | 2G |
| Corn | 9C | 7U,9C | 0 | 1C,5H | 1C | 0 | 3U,9G | 0 |
| Soybean | 9C | 4C,9G | 0 | 2C,6H | 2C,8H | 1H | 3C,9G | 2C,8H |
| Wheat | 2U,9G | 2C | 0 | 0 | 0 | 0 | 0 | 0 |
| Wild Oats | 3C,9G | 2C,4G | 0 | 0 | 0 | 0 | 0 | 0 |
| Rice | 6C,9G | 5C,9G | 0 | 4G | 4G | 0 | 1C,6G | 0 |
| Barnyardgrass | 9C | 5C,8H | 0 | 2C,4H | 2H | 0 | 4H | 0 |
| Crabgrass | 9C | 3C,9G | 0 | 0 | 0 | 0 | 0 | 0 |
| Morningglory | 4C,9H | 4C,9H | 0 | 3C,7H | 3C,8G | 2C,7H | 3C,9G | 6C,9G |
| Cocklebur | 4C,9H | 4C,9G | 0 | 3C,9G | 4C,9G | 4G | 3C,9H | 9C |
| Cassia | 5C,7H | 4C,6H | 0 | 3C | 1C,3G | 1C | 0 | 5C,8G |
| Nutsedge | 2C,4G | 3G,5X | 0 | 8G | 1C,8G | 0 | 0 | 0 |

| Rate kg/ha | Cmpd. 1<br>0.1 | Cmpd. 2<br>0.1 | Cmpd. 3<br>0.1 | Cmpd. 4<br>0.1 | Cmpd. 5<br>0.1 | Cmpd. 6<br>0.1 | Cmpd. 7<br>0.1 | Cmpd. 8<br>0.05 | Cmpd. 9<br>0.05 | Cmpd. 10<br>0.05 |
|---|---|---|---|---|---|---|---|---|---|---|
| | | | | PRE-EMERGENCE | | | | | | |
| Sorghum | 7C,9H | 6C,9H | 10H | 1C,9H | 5C,9H | 7C,9H | 0 | 8G,5G | 9G,9C | 9G,9C |
| Corn | 2U,9G | 10E | 10E | 3C,9H | 9H | 9H | 3G | 6G | 9G | 9G,9C |
| Soybean | 9H | 9H | 9H | 9H | 9H | 9H | 1C,2H | 8G,5H | 9G,5H | 8G,5C |

TABLE A-continued

| | | | | | | | | | |
|---|---|---|---|---|---|---|---|---|---|
| Wheat | 5G | 5C,9H | 1C,9H | 3G | 0 | 8G | 0 | 0 | 7G | 7G |
| Wild Oats | 1U,9G | 5C,9H | 4C,9H | 8G | 1C,7G | 3C,9G | 0 | 5G,3H | 8G,6C | 7G,5H |
| Rice | 10E | 10E | 10E | 10E | 10E | 10E | 1C | 8G,8C | 8G,8C | 10E |
| Barnyardgrass | 5C,9H | 9C | 3C,9H | 7C,9H | 2C,9H | 7C,9H | 0 | 8G,5H | 9G,6C | 8G,5H |
| Crabgrass | 9C | 6C,9G | 2C,8G | 2C,5G | 2C,6G | 1C,6G | 0 | 3G | 5G,3H | 3G |
| Morningglory | 9G | 9G | 9C | 9C | 9C | 9C | 1C,3G | 8G,5C | 8G,9C | 8G,9C |
| Cocklebur | 9H | 9H | 9H | 9H | 9H | 9H | 8H | 8G,3H | 9G,9P | 9G,9P |
| Cassia | 9C | 5C,9G | 6C,9G | 6C,9G | 6C,9G | 6C,9G | 2C,2H | 9G,5C | 9G,9C | 8C,9G |
| Nutsedge | 10E | 10E | 10E | 1C,7G | 1C,6G | 6G | 0 | 10E | 10E | 10E |

| | Cmpd. 11 | Cmpd. 12 | Cmpd. 13 | Cmpd. 14 | Cmpd. 15 | Cmpd. 16 | Cmpd. 17 | Cmpd. 18 | Cmpd. 19 | Cmpd. 20 |
|---|---|---|---|---|---|---|---|---|---|---|
| Rate kg/ha | 0.05 | 0.05 | 0.05 | 0.05 | 0.1 | 0.1 | 0.05 | 0.05 | 0.05 | 0.05 |
| | | | | PRE-EMERGENCE | | | | | | |
| Sorghum | 0 | 0 | 0 | 0 | 0 | 0 | 3C,6G | 5C,8G | 7C,7G | 7C,8G |
| Corn | 0 | 0 | 0 | 0 | 0 | 0 | 7C,8G | 7C,8G | 7C,6G | 7C,8G |
| Soybean | 0 | 0 | 0 | 0 | 0 | 0 | 7C,8G | 7C,8G | 7C,6G | 6C,7G |
| Wheat | 0 | 0 | 0 | 0 | 0 | 0 | 0 | 3C,5G | 0 | 0 |
| Wild Oats | 0 | 0 | 0 | 0 | 0 | 0 | 2C | 7C,6G | 2C,6G | 2C,5G |
| Rice | 3G | 0 | 0 | 0 | 0 | 0 | 10E | 8C,8G | 8C,7G | 10E |
| Barnyardgrass | 0 | 0 | 0 | 0 | 0 | 0 | 7C,8G | 7C,7G | 7C,5G | 7C,7G |
| Crabgrass | 0 | 0 | 0 | 0 | 0 | 0 | 2C,2G | 3G,2C | 0 | 4C,5G |
| Morningglory | 7G | 0 | 3C,9G | 4C,9G | 0 | 0 | 7C,7G | 10C | 7C,6G | 10C |
| Cocklebur | 5H | 0 | 8H,3C | 7H,3C | 0 | 0 | 8C,7G | 3C,5G | 5C,6G | 10C |
| Cassia | 0 | 0 | 2C | 0 | 0 | 0 | 8C,8G | 7C,6G | 5C,4G | 5G,6C |
| Nutsedge | 0 | 0 | 0 | 0 | 0 | 0 | 10E | 10E | 10E | 0 |

| | Cmpd. 21 | Cmpd. 22 | Cmpd. 30 | Cmpd. 31 | Cmpd. 32 | Cmpd. 33 | Cmpd. 34 | Cmpd. 35 | Cmpd. 36 |
|---|---|---|---|---|---|---|---|---|---|
| Rate kg/ha | 0.05 | 0.1 | 0.05 | 0.05 | 0.05 | 0.05 | 0.05 | 0.1 | 0.05 |
| | | | | PRE-EMERGENCE | | | | | |
| Sorghum | 7C,8G | 0 | 1C,9H | 4C,9G | 3C,9H | 2C,9G | 2C,7G | 0 | 2C,9H |
| Corn | 8C,8G | 0 | 1C,9G | 2C,9G | 2C,9H | 1C,9G | 1C,8G | 0 | 2C,5G |
| Soybean | 7C,6G | 0 | 1C,9G | 8H | 3C,7H | 9H | 1C,9H | 0 | 1C,4H |
| Wheat | 0 | 0 | 9G | 9G | 3C | 0 | 0 | 0 | 0 |
| Wild Oats | 5C,6G | 0 | 8G | 2C,9H | 1C,9G | 1C,5G | 0 | 0 | 1C,6G |
| Rice | 10E | 0 | 10E | 2C,9H | 10E | 9H | 2C,5G | 0 | 3C,9H |
| Barnyardgrass | 8C,8G | 0 | 5C,9H | 2C,9H | 2C,9H | 3C,8H | 1C,5H | 0 | 2C,8H |
| Crabgrass | 5C,7G | 0 | 2C,8G | 2C,9G | 1C,3G | 1C,3G | 0 | 0 | 1C |
| Morningglory | 10C | 0 | 9G | 9C | 9G | 1C,9H | 2C,9G | 0 | 9G |
| Cocklebur | 10C | 0 | 9H | 9H | 9H | 9H | 9H | 0 | 9H |
| Cassia | 7C,6G | 0 | 2C,9G | 2C,9G | 2C,9G | 9G,3C | 6C,9G | 0 | 2C,8G |
| Nutsedge | 7C,5G | 0 | 10E | 10E | 10E | 1C,9G | 3G | 0 | 9G |

| | Cmpd. 37 | Cmpd. 38 | Cmpd. 39 | Cmpd. 40 | Cmpd. 23 | Cmpd. 24 | Cmpd. 25 | Cmpd. 26 | Cmpd. 27 | Cmpd. 28 |
|---|---|---|---|---|---|---|---|---|---|---|
| Rate kg/ha | 0.05 | 0.05 | 0.05 | 0.4 | 0.05 | 0.05 | 0.05 | 0.05 | 0.05 | 0.4 |
| | | | | PRE-EMERGENCE | | | | | | |
| Sorghum | 2C,9H | 2C,9H | 1C,7G | 0 | 0 | 4H | 0 | 0 | 0 | 0 |
| Corn | 2C,8H | 2C,7H | 1C,3G | 0 | 0 | 0 | 0 | 0 | 0 | 0 |
| Soybean | 2C,5G | 2G | 1C | 1H | 1H | 1C,1H | 0 | 0 | 0 | 0 |
| Wheat | 3G | 0 | 0 | 0 | 0 | 0 | 0 | 0 | 0 | 0 |
| Wild Oats | 1C,8G | 1C,6G | 0 | 0 | 0 | 0 | 0 | 0 | 0 | 0 |
| Rice | 2C,8H | 2C,6G | 2C | 0 | 0 | 2C | 0 | 0 | 0 | 0 |
| Barnyardgrass | 2C,9H | 3C,5G | 1C,4H | 0 | 0 | 0 | 0 | 0 | 0 | 0 |
| Crabgrass | 1C,3G | 1C | 1C | 2G | 0 | 1C | 0 | 0 | 0 | 0 |
| Morningglory | 9G | 1C,6G | 9G | 3G | 0 | 0 | 0 | 0 | 0 | 0 |
| Cocklebur | 9H | 9H | 9H | 5H | 0 | 2C | 0 | 0 | 9H | 0 |
| Cassia | 2C,8H | 1C | 2C,9H | 0 | 0 | 3G | 0 | 0 | 0 | 0 |
| Nutsedge | 9G | 5G | 2G | 0 | 0 | 3G | 0 | 0 | 0 | 0 |

| | Cmpd. 29 | Cmpd. 41 | Cmpd. 42 | Compound 43 | | Compound 44 | | Cmpd. 45 | Cmpd. 46 | Cmpd. 47 | Cmpd. 48 |
|---|---|---|---|---|---|---|---|---|---|---|---|
| Rate kg/ha | 0.05 | 0.4 | 0.4 | 2 | 6 | 2 | 6 | 0.05 | 0.05 | 0.05 | 0.05 |
| | | | | PRE-EMERGENCE | | | | | | | |
| Sorghum | 0 | 5C,9H | 5C,9H | 0 | 1C,5G | 0 | 2C | 3C,9H | 10H | 3C,9H | 1C |
| Corn | 0 | 2U,9G | 2C,9G | 0 | 2C,5G | 0 | 1C,2G | 2C,8G | 9G | 9G | 1C,3G |
| Soybean | 0 | 9H | 4C,8H | 0 | 0 | 0 | 0 | 2C,2H | 9H | 9H | 1H |
| Wheat | 0 | 8G | 2C,8G | 0 | 0 | 0 | 0 | 0 | 5G | 0 | 0 |
| Wild Oats | 0 | 4C,8G | 2C,8G | 0 | 1C,4G | 0 | 0 | 3C,8H | 3C,9H | 9H | 3G |
| Rice | 0 | 10E | 10E | 0 | 1C | 0 | 1C | 4C,8H | 5C,9H | 10E | 1C |
| Barnyardgrass | 0 | 4C,9H | 4C,9G | 0 | 5C,8H | 0 | 5C | 3C,7H | 6C,9H | 4C,9H | 2C |
| Crabgrass | 0 | 5G | 1C,4G | 0 | 2G | 0 | 0 | 1C,5G | 3C,8H | 2C,8G | 0 |
| Morningglory | 0 | 9C | 9C | 0 | 3C | 0 | 2C | 3C,9H | 2C,9H | 2H,9G | 1C |
| Cocklebur | 0 | 9H | 9H | 0 | 2C,8H | 0 | 5H | 2C,8H | 9H | 9H | 0 |
| Cassia | 0 | 4C,9G | 3C,7G | 0 | 3G | 0 | 5G | 5C | 3C,9G | 5C,9G | 1C |
| Nutsedge | 0 | 1C,9G | 8G | 0 | 0 | 0 | 0 | 10E | 10E | 10E | 0 |

| | Cmpd. 49 | Cmpd. 50 | Cmpd. 51 | Cmpd. 52 | Cmpd. 53 | Cmpd. 54 | Cmpd. 55 | Cmpd. 56 |
|---|---|---|---|---|---|---|---|---|
| Rate kg/ha | 0.05 | 0.05 | 0.05 | 0.05 | 0.05 | 0.05 | 0.05 | 0.05 |
| | | | | PRE-EMERGENCE | | | | |
| Sorghum | 10H | 5C,9H | 0 | 2C,6G | 1C,4G | 0 | 1C,4G | 4G |
| Corn | 3C,9G | 2C,9G | 0 | 3C,7G | 1C,4G | 1C,5G | 3C,7G | 0 |
| Soybean | 3C,5H | 2C,5H | 0 | 1C | 1C | 1H | 1C | 0 |

TABLE A-continued

| | | | | | | | | |
|---|---|---|---|---|---|---|---|---|
| Wheat | 1C | 2C | 0 | 0 | 0 | 0 | 0 | 0 |
| Wild Oats | 3C,9G | 2C,5G | 0 | 0 | 0 | 0 | 0 | 0 |
| Rice | 9H | 9H | 0 | 1C,3G | 1C,4G | 2G | 1C,3G | 2G |
| Barnyardgrass | 3C,9H | 3C,9H | 0 | 2C,8H | 3C | 2C | 1C | 2C |
| Crabgrass | 1C | 1C | 0 | 1C | 1C | 0 | 0 | 0 |
| Morningglory | 4C,9H | 2C,9G | 0 | 6H,2C | 8G,2C | 0 | 8H,2C | 9C |
| Cocklebur | — | 9H | 0 | 3C,8H | — | 0 | — | 9H |
| Cassia | 3C,3H | 2C,3H | 0 | 1C | 0 | 0 | 0 | 5C,9G |
| Nutsedge | 1C | 3G | 0 | 1C,8G | 9G | 0 | 0 | 5G |

It is noted that certain compounds such as 15, 16, 22–25, 28 and 29 show little if any activity at the levels tested. It is thought that they would demonstrate herbicidal activity at higher rates.

viously for Test A. The data are summarized in Table B.

TABLE B

| | PRE-EMERGENCE ON FALLSINGTON SILT LOAM | | | | | | | | | | |
|---|---|---|---|---|---|---|---|---|---|---|---|
| | Compound 1 | | Compound 2 | | Compound 3 | | | | Compound 36 | | Compound 39 | |
| Rate kg/ha | 0.03 | 0.12 | 0.03 | 0.12 | 0.007 | 0.015 | 0.03 | 0.12 | 0.06 | 0.25 | 0.06 | 0.25 |
| Crabgrass | 7G,2H | 8G,3H | 7G,3H | 8G,3H | 0 | 0 | 5G | 6G | 2G | 4G | 2G | 2G |
| Barnyardgrass | 8G,3H | 9G,9C | 9G,8C | 10C | 2G | 2G | 8G,3H | 9G,9C | 4G | 6G,5H | 4G | 5G |
| Sorghum | 9G,9C | 10C | 10C | 10E | 2G | 4G | 10C | 10E | 6G,3H | 8G,5H | 4G | 4G,2H |
| Wild Oats | 6G | 10C | 8G,5C | 9G,9C | 0 | 0 | 10C | 10C | 4G | 4G | 3G | 3G |
| Johnsongrass | 8G,7C | 10C | 9G,9C | 10C | 0 | 3G | 10C | 10C | 4G,3H | 6G,3H | 4G | 3G |
| Dallisgrass | 7G | 9G,9C | 8G,3H | 8G,3H | 0 | 3G | 6G | 8G,3H | 4G | 5G | 3G | 0 |
| Giant foxtail | 6G,3C | 8G,5C | 5G,3C | 10C | 0 | 3G | 3C | 7G,3C | 4G | 6G,3H | 0 | 2G |
| Ky. bluegrass | 8G,9C | 10C | 8G,9C | 10C | 0 | 2G | 10C | 8G,8C | 6G | 7G | 2G | 4G |
| Cheatgrass | 8G,9C | 9G,9C | 10E | 10E | 0 | — | 10E | 10E | 6G | 7G | 0 | 3G |
| Sugarbeets | 10C | 10C | 10C | 10C | — | 4G | 10C | 10C | 6G,6C | 8G,9C | 9G,8C | 10C |
| Corn | 5G,3U | 8G,5H | 7G,5H | 10C | 0 | 0 | 10C | 10C | 3G | 4G | 2G | 4G |
| Mustard | 10C | 10C | 10C | 10C | 5G | 7G,3C | 10C | 10C | 10E | 10E | 8G,8C | 8G,9C |
| Cocklebur | 6G | — | 5G | 10C | 0 | 0 | 7G | 8G,5H | — | 8G,7C | 8G,5H | 10C |
| Pigweed | 10C | 10E | 7G | 10E | 0 | 10E | 9G,9C | 10C | 5G,5C | 9G,9C | 4G | 6G,4C |
| Nutsedge | 10E | 10E | 6G | 10E | 0 | 0 | 10E | 10E | 7G | 10E | 4G | 6G |
| Cotton | 8G | 9G,5C | 6G,3H | 9G,8C | 0 | 0 | 8G,3C | 9G,7C | 4G | 8G,3H | 8G,3H | 9G,5C |
| Morningglory | 5G | 9G,9C | 7G | 9G,5C | 3G | 3G | 8G | 9G,7C | 4G | 8G,9C | 9G | 9G,3C |
| Cassia | 8G,8C | 10C | 7G,4C | 9G,9C | 0 | 0 | 9G,8C | 9G,8C | 6G | 8G,8C | 5G,3C | 7G,8C |
| Teaweed | 6G | 9G,8C | 6G,3H | 8G,6C | — | 0 | 4G | 10C | 5G,3C | 6G,3C | 6G,2C | 6G,3C |
| Velvetleaf | 9G,8C | 10C | 8G,8C | 9G,9C | 0 | 0 | 8G,5E | 9G,8C | 5G,3H | 8G,8C | 7G,3H | 8C,9C |
| Jimsonweed | 7G,3C | 9G,8C | 9G,9C | 9G,9C | 0 | 0 | 8G,8C | 9G,9C | 3G | 5G,5C | 7G,3C | 8G,5C |
| Soybean | 8G,5H | 9G,8C | 7G,5H | 9G,8C | 0 | 0 | 8G,5H | 9G,8C | 2G | 5G,3H | 3G | 4G |
| Rice | 8G,3H | 10E | 8G,7C | 10E | 3G | 6G,3H | 10E | 10E | 3G | 5G | 0 | 0 |
| Wheat | 0 | 3G | 5G | 8G,9C | 0 | 0 | 5G | 7G,3C | 0 | 0 | 0 | 0 |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

Test C

The high herbicidal activity of two of the compounds from within the scope of the invention is evident from the results obtained in this test. The experiment concerned pre-emergence applications on soil. The containers used were 25 cm diameter plastic pots filled with Fallsington silt loam. One set of pots was planted to weeds, the seeds of which were uniformly mixed with the top 1.2 cm layer of soil. The species selected were: johnsongrass (*Sorghum halepense*), barnyardgrass (*Echinochloa crusgalli*), crabgrass (*Digitaria sanguinalis*), giant foxtail (*Setaria faberii*), velvetleaf (*Abutilon theophrasti*), jimsonweed (*Datura stramonium*), mustard (*Brassica arvensis*), and pigweed (*Amaranthus retroflexus*). Another set of pots was planted to the following crops with from one to four species per pot: corn (planting depth 3.7 cm), cotton, soybeans, sunflower, Clinton oats, wheat, Black Valentine beans, rice, sorghum, peas, flax, and peanuts (all at 2.5 cm depth), cucumbers, cabbage, alfalfa, safflower, sugarbeets, tomato, spinach, barley, and Kentucky bluegrass (all at 1.2 cm depth). Immediately after planting, the test chemical was applied to the soil surfaces dissolved in a nonphytotoxic solvent. One pot from the weed phase and one of each of the crop species were left untreated for the purpose of comparison. The treated and untreated pots were promptly watered with approximately 4 mm of simulated rainfall and then held in a greenhouse for several weeks. Visual weed and crop response ratings were made 28 days after treatment utilizing the rating system as described above for Test A. The data are given in Table C.

*bursa-pastoris*), *Matricaria inodora*, black nightshade (*Solanum nigrum*), yellow rocket (*Barbarea vulgaris*), wild mustard (*Brassica kaber*) and wild buckwheat (*Polygonum convolvulus*). The above two pans were treated

TABLE C

PRE-EMERGENCE ON FALLSINGTON SILT LOAM SOIL

| | Compound 1 | | | | Compound 2 | | | |
|---|---|---|---|---|---|---|---|---|
| Rate kg/ha | 0.0035 | 0.0075 | 0.0150 | 0.03 | 0.0075 | 0.015 | 0.030 | 0.06 |
| Corn | | | | 5G,3C | | | | 9G,9C |
| Cotton | | | | 7G,3H | | | | 10E |
| Soybean | | | | 4G,2H | | | | 9G,5H |
| Peanut | | | | 6G | | | | 8G,3H |
| Sunflower | | | | 5G | | | | 9G,5H |
| Oats | | | | 4G | | | | 6G,2C |
| Wheat | | | | 2G | | | | 5G |
| Sorghum | | | | 7G,5H | | | | 10E |
| Sugarbeet | | | | 9G,9C | | | | 10E |
| Pea | | | | 10E | | | | 10E |
| Flax | | | | 6G | | | | 10E |
| Alfalfa | | | | 8G,6C | | | | 8G,6C |
| Bean | | | | 0 | | | | 8G,5H |
| Spinach | | | | 8G,5H | | | | 9G,9C |
| Cabbage | | | | 8G,6C | | | | 8G,7C |
| Tomato | | | | 4G | | | | 5C,8G |
| Rice | | | | 6G | | | | 10E |
| Safflower | | | | 7G,4C | | | | 8G,7C |
| Cucumber | | | | 5G | | | | 9G,5H |
| Ky. bluegrass | | | | 7G | | | | 6G,5H |
| Barley | | | | 3G | | | | 8G,7C |
| Broadleaves | 3G | 4G | 6G,2H | — | 5G,3C | 7G,5C | 9G,8C | — |
| Grasses | 0 | 0 | 2G | — | 6G,3C | 8G,4C | 9G,6C | — |

Test D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pensylvanicum*), tumble mustard (*Sisymbrium altissium*) kochia (*Kochia scoparia*), shepherd's purse (*Capsella* pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data, presented in Table D, indicate that certain compounds from within the scope of the invention have utility for pre- and/or post-emergence weed control in cereal crops such as wheat and barley.

TABLE D

Pre-Emergence

| | Compound 1 | | | | | | Compound 2 | | | | | |
|---|---|---|---|---|---|---|---|---|---|---|---|---|
| Rate kg/ha | 0.002 | 0.008 | 0.008 | 0.015 | 0.03 | 0.06 | 0.002 | 0.008 | 0.008 | 0.015 | 0.03 | 0.06 |
| wheat | 0 | 0 | 0 | 0 | 0 | 2C,3G | 0 | 0 | 0 | 2C,2G | 2C,4G | 4C,6G |
| barley | 0 | 0 | 0 | 1C,6G | 1C,1G | 6C,8G | 0 | 3G | 3C,4G | 5C,7G | 6C,7G | 8C,8G |
| wild oats | 0 | 0 | 0 | 3C,7G | 0 | 8C,8G | 0 | 2C,5G | 2G | 8C,8G | 7C,6G | 9C,8G |
| downy brome | 3G | 2C,5G | 1G | 5C,7G | 2C,7G | 10C | 6G | 7C,7G | 3C,7G | 10C | 7C,8G | 10C |
| cheatgrass | 5G | 4C,7G | 3G | 10C | 5C,8G | 10C | 5C,7G | 10C | 5C,8G | 10C | 10C | 10C |
| blackgrass | 3G | 5C,6G | 2G | 10C | 3C,7G | 10C | 3C,6G | 7C,7G | 3C,7G | 10C | 8C,7G | 10C |
| annual bluegrass | 5G | 2C,6G | 1C,2G | 7C,8G | 5C,7G | 10C | 1C,6G | 7C,7G | 2C,5G | 10C | 5C,6G | 10C |
| green foxtail | 0 | 2G | 3C,4G | 3C,5G | 7C,7G | 9C,8G | 0 | 4C,5G | 2C,4G | 6C,7G | 4C,6G | 9C,9G |
| quackgrass | 3G | 3C,5G | 0 | 8G | 2C,3G | 10C | 4G | 3C,6G | 4G | 8C,9G | 7C,7G | 9C,9G |
| Italian ryegrass | 0 | 3C,5G | 0 | 4G | 1C,3G | 4C,7G | 3G | 5C,7G | 5C,7G | 9C,9G | 7C,8G | 10C |
| ripgut brome | 2G | 2C,4G | 0 | 2C,5G | 0 | 5C,7G | 5G | 6G | 3C,4G | 9C,9G | 6C,7G | 9C,9G |
| Russian thistle | 0 | 0 | 1G | 8C,7G | 2C,3G | 8C,8G | 0 | 1C,1G | 3C,4G | 9C,9G | 5C,6G | 10C |
| tansy mustard | 6G | 8C,8G | 8C,8G | 10C | 10C | 10C | 3C,8G | 8C,9G | 7C,8G | 10C | 9C,9G | 10C |
| smartweed | — | — | — | — | — | — | — | — | — | — | — | — |
| tumble mustard | 3C,8G | 10C | 7C,7G | 10C | 10C | 10C | 7C,8G | 10C | 10C | 10C | 10C | 10C |
| kochia | 1G | 5G | 3G | 9C,8G | 7C,8G | 10C | 2G | 5G | 7C,8G | 8C,9G | 9C,8G | 9C,9G |
| shepherd's purse | 3C,5G | 8C,8G | 9C,8G | 10C | 10C | 10C | 8C,8G | 8C,8G | 10C | 10C | 10C | 10C |
| *Matricaria inodora* | 4G | 7C,8G | 7C,7G | 10C | 7C,8G | 10C | 5C,8G | 7C,8G | 7C,7G | 10C | 7C,8G | 10C |
| black nightshade | 2C,4G | 4C,6G | 6C,7G | 8G | 7C,7G | 3C,8G | 3C,4G | 3C,4G | 5C,6G | 2C,7G | 7C,6G | 5C,8G |
| yellow rocket | 2C,7G | 4C,8G | 10C | 10C | 8C,9G | 10C | 8G | 2C,9G | 7C,7G | 10C | 10C | 10C |
| wild mustard | 5C,6G | 8C,8G | 7C,7G | 10C | 8C,8G | 10C | 7C,8G | 8C,8G | 7C,8G | 10C | 9C,8G | 10C |

TABLE D-continued

| | | | Pre-Emergence | | | | | Post-Emergence | | | | | |
|---|---|---|---|---|---|---|---|---|---|---|---|---|---|
| wild buckwheat | 3G | 2C,4G | 1C,2G | 3C,6G | 3C,4G | 4C,8G | 2C,1G | 3C,4G | 3C,2G | 3C,4G | 4C,5G | 5C,6G | |
| | | Compound 3 | | Compound 36 | | | | Compound 1 | | | | Compound 2 | |
| Rate kg/ha | | 0.008 | 0.03 | 0.015 | 0.06 | 0.002 | 0.008 | 0.008 | 0.015 | 0.03 | 0.06 | 0.002 | 0.008 |
| wheat | | 0 | 1C,2G | 0 | 0 | 0 | 0 | 0 | 0 | 0 | 1C,2G | 0 | 1G |
| barley | | 2G | 7C,6G | 0 | 0 | 0 | 0 | 0 | 3C,5G | 2C,2G | 7C,6G | 0 | 3G |
| wild oats | | 1G | 7C,7G | 0 | 0 | 0 | 1C | 0 | 3C,2G | 2G | 3C,3G | 0 | 2C,5G |
| downy brome | | 4G | 10C | 3G | 6G | 3G | 5C,7G | 4C,5G | 3G | 7C,7G | 3C,4G | 3C,5G | 7C,7G |
| cheatgrass | | 2C,5G | 10C | 7G | 10C | 4C,7G | 8C,7G | 8C,7G | 10C | 10C | 10C | 6C,7G | 10C |
| blackgrass | | 7C,7G | 10C | 6G | 3C,7G | 6G | 4C,5G | 7C,7G | 10C | 10C | 10C | 2C,6G | 7C,7G |
| annual bluegrass | | 3C,4G | 5C,6G | 6G | 7C,7G | 3G | 3C,6G | 3C,5G | 5C,4G | 6C,7G | 10C | 5C,6G | 10C |
| green foxtail | | 2C,3G | 5C,4G | 2G | 3C,5G | 4G | 7C,7G | 7C,7G | 3C,4G | 7C,8G | 7C,6G | 3C,5G | 4C,5G |
| quackgrass | | 0 | 3C,4G | 0 | 2G | 3G | 6G | 2C,3G | 6C,5G | 3C,6G | 7C,6G | 1C,6G | 4C,6G |
| Italian ryegrass | | 3G | 7C,7G | 1G | 3G | 2G | 2G | 0 | 3G | 2C,4G | 4C,5G | 1C,5G | 3C,6G |
| ripgut brome | | 0 | 10C | 2G | 2C,7G | 2G | 5G | 0 | 2G | 2C,3G | 3C,5G | 4G | 1C,7G |
| Russian thistle | | 0 | 7C,7G | 0 | 1G | 2C,3G | 10C | 9C,7G | 10C | 10C | 10C | 5C,4G | 8C,7G |
| tansy mustard | | 4C,5G | 9C,9G | 2G | 2C,5G | 10C | 10C | 10C | 10C | 10C | 10C | 10C | 10C |
| smartweed | | — | — | — | — | — | — | — | — | — | — | — | — |
| tumble mustard | | 7G | 10C | 5G | 3C,7G | 4C,6G | 10C | 10C | 10C | 10C | 10C | 7C,8G | 8C,8G |
| kochia | | 6G | 10C | 0 | 5C,6G | 3G | 4G | 10C | 8C,7G | 10C | 10C | 5G | 10C |
| shepherd's purse | | 7C,7G | 10C | 7G | 3C,8G | 10C | 10C | 10C | 10C | 10C | 10C | 10C | 10C |
| *Matricaria inodora* | | 6C,7G | 7C,7G | 3C,8G | 7C,8G | 7C,7G | 10C | 9C,7G | 10C | 9C,8G | 10C | 10C | 10C |
| black nightshade | | 3C,4G | 5C,6G | 4G | 1C,5G | 4G | 4C,6G | 1C,1G | 0 | 3C,7G | 4C,5G | 2G | 3C,5G |
| yellow rocket | | 7G | 7C,7G | 3C,8G | 10C | 3G | 10C | 10C | 10C | 10C | 10C | 10C | 10C |
| wild mustard | | 5C,7G | 7C,8G | 7C,8G | 10C | 10C | 10C | 10C | 10C | 10C | 10C | 10C | 10C |
| wild buckwheat | | 0 | 2C,3G | 3G | 1C,4G | 2C,4G | 5C,5G | 6C,5G | 10C | 7C,6G | 10C | 2C,2G | 3C,5G |

| | Post-Emergence | | | | | | | |
|---|---|---|---|---|---|---|---|---|
| | Compound 2 | | | | Compound 3 | | Compound 36 | |
| | 0.008 | 0.015 | 0.03 | 0.06 | 0.008 | 0.03 | 0.015 | 0.06 |
| wheat | 1G | 5C,5G | 1C,2G | 7C,7G | 0 | 1C,2G | 0 | 0 |
| barley | 2C,3G | 7C,6G | 4C,6G | 10C | 0 | 4C,6G | 0 | 0 |
| wild oats | 5G | 7C,7G | 5C,6G | 8C,7G | 0 | 7C,5G | 0 | 0 |
| downy brome | 7C,7G | 7C,7G | 8C,7G | 10C | 6C,7G | 7C,7G | 0 | 3G |
| cheatgrass | 10C | 10C | 10C | 10C | 7C,7G | 10C | 1G | 3C,5G |
| blackgrass | 7C,7G | 10C | 10C | 10C | 4C,5G | 10C | 2G | 5C,4G |
| annual bluegrass | 6C,5G | 10C | 10C | 10C | 4C,6G | 5C,7G | 2G | 3G |
| green foxtail | 7C,8G | 6C,6G | 8C,8G | 7C,7G | 2C,4G | 6C,7G | 1G | 2G |
| quackgrass | 6G | 7C,6G | 4C,6G | 10C | 2C,3G | 4C,6G | 0 | 0 |
| Italian ryegrass | 3C,6G | 10C | 5C,7G | 10C | 3C,6G | 5C,6G | 0 | 0 |
| ripgut brome | 3G | 4C,6G | 4C,4G | 9C,8G | 1C,2G | 3C,4G | 0 | 2G |
| Russian thistle | 10C | 10C | 10C | 10C | 3C,2G | 10C | 0 | 2G |
| tansy mustard | 10C | 10C | 10C | 10C | 8C,7G | 10C | 5C,4G | 7C,8G |
| smartweed | — | — | — | — | — | — | — | — |
| tumble mustard | 10C | 10C | 10C | 10C | 10C | 10C | 10C | 10C |
| kochia | 10C | 7C,6G | 10C | 10C | 4G | 10C | 0 | 0 |
| shepherd's purse | 10C | 10C | 10C | 10C | 9C,8G | 10C | 7C,8G | 10C |
| *Matricaria inodora* | 7C,7G | 10C | 8C,7G | 10C | 6C,5G | 9C,8G | 7C,7G | 9C,8G |
| black nightshade | 1C,1G | 0 | 3C,4G | 2G | 4G | 8C,8G | 2G | 4C,5G |
| yellow rocket | 8C,8G | 10C | 10C | 10C | 2C,5G | 10C | 7C,7G | 10C |
| wild mustard | 10C | 10C | 10C | 10C | 10C | 10C | 10C | 10C |
| wild buckwheat | 6C,6G | 10C | 7C,8G | 10C | 2C,2G | 5C,6G | 1C,2G | 5C,4G |

Test E

Test samples were formulated and applied directly to the paddy water three days after transplanting of rice. The test was maintained in a greenhouse, and plant response ratings were taken at the stated intervals after application. The data indicate:

| | Compound 1 | | | |
|---|---|---|---|---|
| Rate g/ha | Rice 4 Days | Rice 4 Weeks | Barnyard-grass* 4 Weeks | Water Chestnut** 4 Weeks |
| 1 | 0 | 0 | 0 | 7G |
| 4 | 0 | 0 | 0 | 8G |
| 8 | 0 | 0 | 0 | 9G |

| | Compound 36 | | | | |
|---|---|---|---|---|---|
| Rate, g/ha | Rice 1 Week | Rice 8 Weeks | Barnyard-grass* 8 Weeks | Water Chestnut** 8 Weeks | Arrow-head*** 8 Weeks |
| 25 | 0 | 0 | 0 | 10C | 0 |
| 100 | 0 | 0 | 0 | 10C | 0 |

*Echinochloa spp.
**Eleocharis spp.
***Sagittaria spp.

It may be seen that compounds from within the scope of the invention can be used for selective weed control in rice.

Test F

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table F.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugarbeets, and mustard. All plants were sprayed approximately 14 days after planting.

Some of the compounds tested by this procedure are useful for the post-emergence control of weeds in wheat. Compound 39 has utility for the post-emergence control of weeds in soybeans and corn.

another pot of equal size the following broadleaf plant species were grown: sugarbeets, velvetleaf, Sesbania, Cassia, mustard, morningglory, alfalfa, jimsonweed, and cocklebur. The plant foliage and surrounding soil were treated with the test chemical dissolved in a non-phytotoxic solvent as an overall spray at the rate of 0.015 kg/ha, when the plants were 17 days old. Visual ratings of herbicidal effects were made 22 days after treatment utilizing the rating system described for Test A.

TABLE G

| Rate | 0.015 |
| --- | --- |
| Soybeans | 0 |
| Sugarbeets | 9G |
| Velvetleaf | 9G,9C |
| Sesbania | 8G,8C |
| Cassia | 7G,4C |
| Mustard | 10C |
| Morningglory | 9G,9C |
| Alfalfa | 8G,4C |
| Jimsonweed | 0 |
| Cocklebur | 10P,2C |

TABLE F

Over-the-Top Soil/Foliage Treatment

| | Compound 1 | | | | Compound 2 | | Compound 3 | | | | Compound 36 |
| --- | --- | --- | --- | --- | --- | --- | --- | --- | --- | --- | --- |
| Rate kg/ha | 0.06 | 0.015 | 0.007 | 0.003 | 0.06 | 0.015 | 0.06 | 0.015 | 0.007 | 0.003 | 0.12 |
| Soybeans | 10G,7C | 10G,7C | 9G,5C | 9G,5C | 9C | 10G,8C | 10G,6C | 10G,4C | 9G,7C | 10G,5C | 10C |
| Velvetleaf | 10G,7C | 8G,3C | 9G,9C | 10G,9C | 10G,4C | 5G | 7G,2C | 5G | 8G,8C | 7G | 10C |
| Sesbania | 9C | 9C | 10C | 10C | 10C | 9C | 9C | 9C | 8G,5C | 9G,8C | 10C |
| Cassia | 10G,7C | 8G,2C | 9G,5C | 10G,5C | 10G,7C | 7G,3C | 10G,7C | 5G,3C | 10G,5C | 8G,4C | 10C |
| Cotton | 10G,7C | 7G,3C | 9G,9C | 10C | 10G,6C | 7G,3C | 10G,6C | 10G,6C | 10C | 8G,2C | 9G,9C |
| Morningglory | 10G,5C | 9G,4C | 10G,8C | 10G,8C | 10C | 8G,2C | 9G,4C | 9G,3C | 10G,8C | 7G,1H | 10C |
| Alfalfa | 9C | 5C | 6G,2C | 6G,2C | 10C | 7C | 9C | 8C | 7G | 6G,2C | 9G |
| Jimsonweed | 9C | 7G,3C | 0 | 0 | 10C | — | 9G,3C | — | — | 0 | 0 |
| Cocklebur | 10G,7C | 9G,3C | 7G | 5G | 10G,8C | 10G,7C | 10G,7C | 10G,7C | 4G,5C | 3G | 10C |
| Corn | 10C | 9G,7C | 8G,2H | 9G,1H | 10C | 10G,7U | 10C | 9G,6C | 9G | 9G,1H | 2G,1C |
| Crabgrass | 8G,4C | 2C | 5G | 0 | 10C | 6G,1C | 7G,4C | 0 | 5G,1C | 0 | 5G |
| Rice | 8G,3C | 3G,1C | 8G,5C | 7G,2C | 10C | 6G,3C | 8G,5C | 7G,3C | 9G,7C | 9G,7C | 5G |
| Nutsedge | 10C | 10C | 5G | 3G | 10C | 2C | 9G,4C | 9G,3C | 7G | 5G | 7G,5C |
| Barnyardgrass | 10C | 10C | 9G,4C | 9G,2C | 10C | 6G,3C | 10C | 9C | 9G,4C | 9G,2C | 9G,5C |
| Wheat | 0 | 0 | 0 | 1G | 9C | 1C | 8C | 1C | 6G | 3G | 2G |
| Giant foxtail | 10G,3C | 7G,3C | 5G | 5G | 10C | — | — | — | 0 | 0 | 3G,2C |
| Wild Oats | 6G | 3G | 3G | 3G | 10C | 5C,3C | 10C | 7G,3C | 5G | 4G | 3G |
| Sorghum | 10C | 9C | 8G,3C | 7G,4U | 10C | 8G,5C | 10C | 9C | 7G,3U | 9G,6U | 7G,3C |
| Mustard | — | — | 10C | 10C | — | — | — | — | 10C | 9G,9C | 10C |
| Sunflower | — | — | 10C | 10C | — | — | — | — | 10C | 10G,9C | 10C |
| Sugarbeets | — | — | 10C | 9G,9C | — | — | — | — | 10C | 9G,9C | 9G,3C |

| | | Compound 36 | | | Compound 39 | | | | | |
| --- | --- | --- | --- | --- | --- | --- | --- | --- | --- | --- |
| | Rate kg/ha | 0.06 | 0.015 | 0.12 | 0.06 | 0.03 | 0.015 | 0.015 | 0.015 | 0.007 |
| | Soybeans | 9G,9C | 9G,7C | 10G,7C | 9G,9C | 4G | 0 | 0 | 3G | 0 |
| | Velvetleaf | 10C | 8G,7C | 9G,7C | 8G,5C | 10G,5C | 8G,4C | 8G,3C | 8G,3C | 7G,3C |
| | Sesbania | 10C | 10C | 10C | 9G,4C | 10G,7C | 8G,6C | 9G,4C | 5G,4C | 7G,4C |
| | Cassia | 9G,3C | 8G,3C | 9G,7C | 5G,5C | 8G,5C | 5G,5C | 8G,4C | 4G,6C | 5G,3C |
| | Cotton | 8G,8C | 4G,4C | 9G,7C | 9G,6C | 9G,5C | 8G,4C | 8G,4C | 8G,4C | 6G,3C |
| | Morningglory | 10C | 8G,4C | 9G,8C | 9G,5C | 9G,4C | 9G,5C | 9G,4C | 10G,3C | 9G,6C |
| | Alfalfa | 5G,3C | 7G | 9G,8C | 10C | 9G,5C | 5G,2C | 9G,5C | 7G | 7G,3C |
| | Jimsonweed | 0 | 0 | 0 | — | — | — | 8G | 2C | — |
| | Cocklebur | 10C | 10C | 10G,7C | 10G,5C | 10G,5C | 9G,5C | 10G,5C | 10G,4C | 9G,4C |
| | Corn | 1G,2C | 1G,1C | 0 | 0 | 3G,2C | 0 | 1G,2C | 0 | 2G |
| | Crabgrass | 0 | 0 | 0 | 0 | 0 | 0 | 0 | 0 | 0 |
| | Rice | 4G | 2G | 0 | 0 | 4G | 1G | 3G | 0 | 2G |
| | Nutsedge | 7G,5C | 0 | 1G | 0 | 3G | 0 | 0 | 0 | 5G |
| | Barnyardgrass | 8G,5C | 6G,2C | 0 | 0 | 3G | 0 | 0 | 0 | 2G |
| | Wheat | 0 | 0 | 0 | 0 | 0 | 0 | 0 | 0 | 0 |
| | Giant foxtail | 2C | 0 | 0 | 0 | 2G | 0 | 2G | 0 | 1G |
| | Wild Oats | 0 | 0 | 0 | 0 | 2G | 0 | 1G | 2G | 0 |
| | Sorghum | 5G,2C | 2G,2C | 0 | 0 | 5G | 0 | 4G | 5G | 3G |
| | Mustard | 10C | 10C | 10C | 10C | 10G,5C | 10G,5C | 10G,5C | 9G | 10G,5C |
| | Sunflower | 10C | 10C | 10C | 10C | 10G,8C | 10G,8C | 10G,8C | 10C | 10G,8C |
| | Sugarbeets | 9G,5C | 8G | 10G,5C | 10C | 9G,3C | 10G,5C | 9G,3C | 9G | 10G,4C |

Test G

This test demonstrates the broadleaf herbicidal properties of compound 39. Approximately 12 soybean plants were grown in a 25 cm. diameter plastic pot. In The data indicate that the compound tested provides excellent post-emergence control of broadleaved weeds in soybeans.

Test H

Test samples of compound 17 were formulated in a non-phytotoxic solvent and applied to the water surface of tub-paddies, three days after transplanting of rice plants into the paddies. The paddy soil contained various weed propagules which were sprouting (except for Scirpus, as explained below). The paddies were maintained in a greenhouse, and plant response ratings (TABLE) were taken about six weeks after application.

TABLE H

| Rate, g ai/ha | Rice | Barnyard-grass* | Water Chestnut* | Arrow-head* | Scirpus* |
|---|---|---|---|---|---|
| 2.5 | 0 | 9E | 7G,2C | 6G,3H | — |
| 10 | 0 | 10E | 10C | 9G,7C | — |
| 20 | 0 | 10E | 9G,9C | 10G,2C | — |

*Echinochloa sp., Eleocharis sp., Saqittaria sp., and Scirpus sp. Scirpus failed to become established and could not be rated.

The data above demonstrate excellent control of weeds that are often found in rice cultures and excellent rice tolerance to the application.

What is claimed is:
1. A compound of the formula

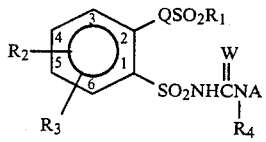

where
W is O or S;
Q is O or NR$_5$;
R$_1$ is C$_1$-C$_4$ alkyl, C$_1$-C$_4$ alkyl substituted with 1-3 atoms of F, Cl or Br, CH$_2$CH$_2$OCH$_3$, CH$_2$CH$_2$CH$_2$OCH$_3$ or

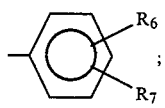

R$_2$ is H, F, Cl, Br, OCH$_3$, NO$_2$, CF$_3$ or C$_1$-C$_2$ alkyl;
R$_3$ is H, F, Cl, Br or CH$_3$;
R$_4$ is H, CH$_3$ or OCH$_3$;
R$_5$ is C$_1$-C$_4$ alkyl;
R$_6$ and R$_7$ are independently H, F, Cl, Br, CH$_3$, CF$_3$, NO$_2$ or OCH$_3$;
A is

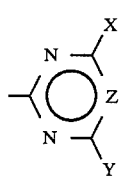

X is NH$_2$, N(CH$_3$)$_2$, NHCH$_3$, C$_1$-C$_4$ alkyl, C$_1$-C$_4$ alkyl substituted with 1-3 atoms of F, Cl or Br, CH$_2$OCH$_3$, CH$_2$OCH$_2$CH$_3$, C$_1$-C$_4$ alkoxy, C$_1$-C$_4$ alkylthio, C$_3$-C$_4$ alkenyloxy, C$_3$-C$_4$ alkynyloxy,
OCH$_2$CH$_2$OCH$_3$ or C$_2$-C$_4$ alkoxy substituted with 1-3 atoms of F, Cl or Br;
n is 1 or 2;
Y is CH$_3$ or OCH$_3$; and
Z is N;
provided that
(1) when W is S, then R$_4$ is H; and
(2) when R$_4$ is OCH$_3$, then Q is O.

2. A compound of claim 1 where R$_5$ is CH$_3$, W is O, and R$_4$ is H or CH$_3$.

3. A compound of claim 2 where R$_1$ is C$_1$-C$_4$ alkyl, CF$_3$, CH$_2$CH$_2$OCH$_3$ or CH$_2$CH$_2$CH$_2$OCH$_3$.

4. A compound of claim 3 where R$_2$ is H or Cl.

5. A compound of claim 4 where R$_3$ is H.

6. A compound of claim 5 where R$_1$ is C$_1$-C$_3$ alkyl or CF$_3$, and Q is O.

7. A compound of claim 6 where R$_4$ is H.

8. A compound of claim 7 where X and Y are independently CH$_3$ or OCH$_3$, and R$_1$ is CH$_3$.

9. A compound of claim 1 wherein:
Q is

R$_5$ is CH$_3$ or CH$_3$CH$_2$;
R$_1$ is C$_1$-C$_3$ alkyl or CF$_3$;
R$_2$ and R$_3$ are H;
X is CH$_3$, OCH$_3$, N(CH$_3$), CH$_2$OCH$_3$, OCH$_2$CH$_3$ or OCH$_2$CF$_3$; and
Y is CH$_3$ or OCH$_3$.

10. The compound of claim 1, N-[(4,6-dimethoxy-1,3,5-triazin-2-yl)aminocarbonyl]-2-hydroxybenzenesulfonamide, methanesulfonate.

11. The compound of claim 1, 2-hydroxy-N-[(4-methoxy-6-methyl-1,3,5-triazin-2-yl)aminocarbonyl]-benzenesulfonamide, methanesulfonate.

12. The compound of claim 1, N-[(4,6-dimethoxy-1,3,5-triazin-2-yl)aminocarbonyl]-2-hydroxybenzenesulfonamide, methanesulfonate.

13. The compound of claim 1, N-[(4,6-dimethoxy-1,3,5-triazin-2-yl)(methyl)aminocarbonyl]-2-hydroxybenzenesulfonamide, methanesulfonate.

14. The compound of claim 1, 2-hydroxy-N-[(4-methoxy-6-methyl-1,3,5-triazin-2-yl)aminocarbonyl]-benzenesulfonamide, 1-propanesulfonate, which shows selectivity on soybeans.

15. A composition suitable for controlling the growth of undesired vegetation which comprises an effective amount of a compound of claim 1 and at least one of the following: surfactant, solid or liquid diluent.

16. A composition suitable for controlling the growth of undesired vegetation which comprises an effective amount of a compound of claim 2 and at least one of the following: surfactant, solid or liquid diluent.

17. A composition suitable for controlling the growth of undesired vegetation which comprises an effective amount of a compound of claim 3 and at least one of the following: surfactant, solid or liquid diluent.

18. A composition suitable for controlling the growth of undesired vegetation which comprises an effective amount of a compound of claim 4 and at least one of the following; surfactant, solid or liquid diluent.

19. A composition suitable for controlling the growth of undesired vegetation which comprises an effective amount of a compound of claim 5 and at least one of the following: surfactant, solid or liquid diluent.

20. A method for controlling the growth of undesired vegetation which comprises applying to the locus to be protected an effective amount of a compound of claim 1.

21. A method for controlling the growth of undesired vegetation which comprises applying to the locus to be protected an effective amount of a compound of claim 2.

22. A method for controlling the growth of undesired vegetation which comprises applying to the locus to be protected an effective amount of a compound of claim 3.

23. A method for controlling the growth of undesired vegetation which comprises applying to the locus to be protected an effective amount of a compound of claim 4.

24. A method for controlling the growth of undesired vegetation which comprises applying to the locus to be protected an effective amount of a compound of claim 5.

25. A compound selected from:

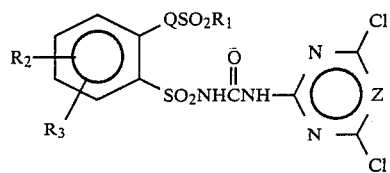

where
Q is O or $NR_5$;
$R_1$ is $C_1$–$C_4$ alkyl, $C_1$–$C_4$ alkyl substituted with 1-3 atoms of F, Cl or Br, $CH_2CH_2OCH_3$, $CH_2CH_2CH_2OCH_3$, or

$R_2$ is H, F, Cl, Br, $OCH_3$, $NO_2$ or $C_1$–$C_2$ alkyl;
$R_3$ is H, F, Cl, Br or $OCH_3$;
$R_5$ is $C_1$–$C_4$ alkyl;
$R_6$ and $R_7$ are independently H, F, Cl, Br, $CH_3$, $CF_3$, $NO_2$ or $OCH_3$; and
Z is N.

* * * * *